US011593842B2

(12) United States Patent
Ibarria et al.

(10) Patent No.: US 11,593,842 B2
(45) Date of Patent: Feb. 28, 2023

(54) SYSTEMS, APPARATUSES, AND METHODS FOR PHYSIOLOGICAL DATA COLLECTION AND PROVIDING TARGETED CONTENT

(71) Applicant: Hygeia Health, LLC, Atlanta, GA (US)

(72) Inventors: Ricardo J. Ibarria, Atlanta, GA (US); Benjamin Davis, Atlanta, GA (US); Andres Rodriguez, Miami, FL (US)

(73) Assignee: Hygeia Health, Inc., Atlanta, GA (US)

( * ) Notice: Subject to any disclaimer, the term of this patent is extended or adjusted under 35 U.S.C. 154(b) by 1129 days.

(21) Appl. No.: 16/201,332

(22) Filed: Nov. 27, 2018

(65) Prior Publication Data

US 2019/0095957 A1    Mar. 28, 2019

Related U.S. Application Data

(60) Division of application No. 14/925,138, filed on Oct. 28, 2015, now abandoned, which is a
(Continued)

(51) Int. Cl.
*A61B 5/00* (2006.01)
*G06Q 30/0251* (2023.01)
(Continued)

(52) U.S. Cl.
CPC ......... *G06Q 30/0269* (2013.01); *A61B 1/227* (2013.01); *A61B 5/0022* (2013.01); *A61B 5/0077* (2013.01); *A61B 5/01* (2013.01); *A61B 5/022* (2013.01); *A61B 5/1455* (2013.01); *A61B 5/6888* (2013.01); *A61B 5/6891* (2013.01); *A61B 5/702* (2013.01); *A61B 5/7271* (2013.01); *A61B 5/742* (2013.01); *A61B 7/02* (2013.01); *G06Q 50/22* (2013.01); *G16H 10/20* (2018.01); *G16H 10/40* (2018.01); *G16H 10/60* (2018.01); *G16H 40/63* (2018.01); *A61B 5/021* (2013.01); *A61B 5/024* (2013.01); *A61B 5/0205* (2013.01); *G16H 20/10* (2018.01)

(58) Field of Classification Search
CPC ..... A61B 1/227; A61B 5/0022; A61B 5/0077; A61B 5/01; A61B 5/0205; A61B 5/021; A61B 5/022; A61B 5/024; A61B 5/1455; A61B 5/6888; A61B 5/6891; A61B 5/702; A61B 5/7271; A61B 5/742; A61B 7/02; G06Q 30/0269; G06Q 50/22; G16H 10/20; G16H 10/40; G16H 10/60; G16H 20/10; G16H 40/63
See application file for complete search history.

(56) References Cited

U.S. PATENT DOCUMENTS

| 2011/0082711 | A1 | 4/2011 | Poeze et al. | |
| 2012/0253837 | A1* | 10/2012 | Cashman | E04H 1/1205 705/2 |

(Continued)

*Primary Examiner* — George Manuel

(57) ABSTRACT

A system, apparatus, and method for physiological data collection, providing targeted content, and facilitating remote diagnostics. In one embodiment, a kiosk contains physiological data collection devices, electronic computing devices, and targeted-content display devices to automatically collect physiological data regarding a patient and display targeted content specifically tailored to that patient based on the collected data.

6 Claims, 20 Drawing Sheets

EXEMPLARY KIOSK, PERSPECTIVE VIEW

Related U.S. Application Data continuation-in-part of application No. 29/505,330, filed on Sep. 17, 2015, now abandoned.

(60) Provisional application No. 62/069,550, filed on Oct. 28, 2014.

(51) Int. Cl.
| | |
|---|---|
| *G06Q 50/22* | (2018.01) |
| *A61B 5/022* | (2006.01) |
| *A61B 5/01* | (2006.01) |
| *A61B 5/1455* | (2006.01) |
| *A61B 7/02* | (2006.01) |
| *A61B 1/227* | (2006.01) |
| *G16H 10/20* | (2018.01) |
| *G16H 10/40* | (2018.01) |
| *G16H 40/63* | (2018.01) |
| *G16H 10/60* | (2018.01) |
| A61B 5/0205 | (2006.01) |
| A61B 5/021 | (2006.01) |
| A61B 5/024 | (2006.01) |
| G16H 20/10 | (2018.01) |

(56) References Cited

U.S. PATENT DOCUMENTS

| | | |
|---|---|---|
| 2013/0101970 A1 | 4/2013 | Mascarenhas |
| 2014/0018779 A1* | 1/2014 | Worrell ................ A61B 90/00 606/1 |

* cited by examiner

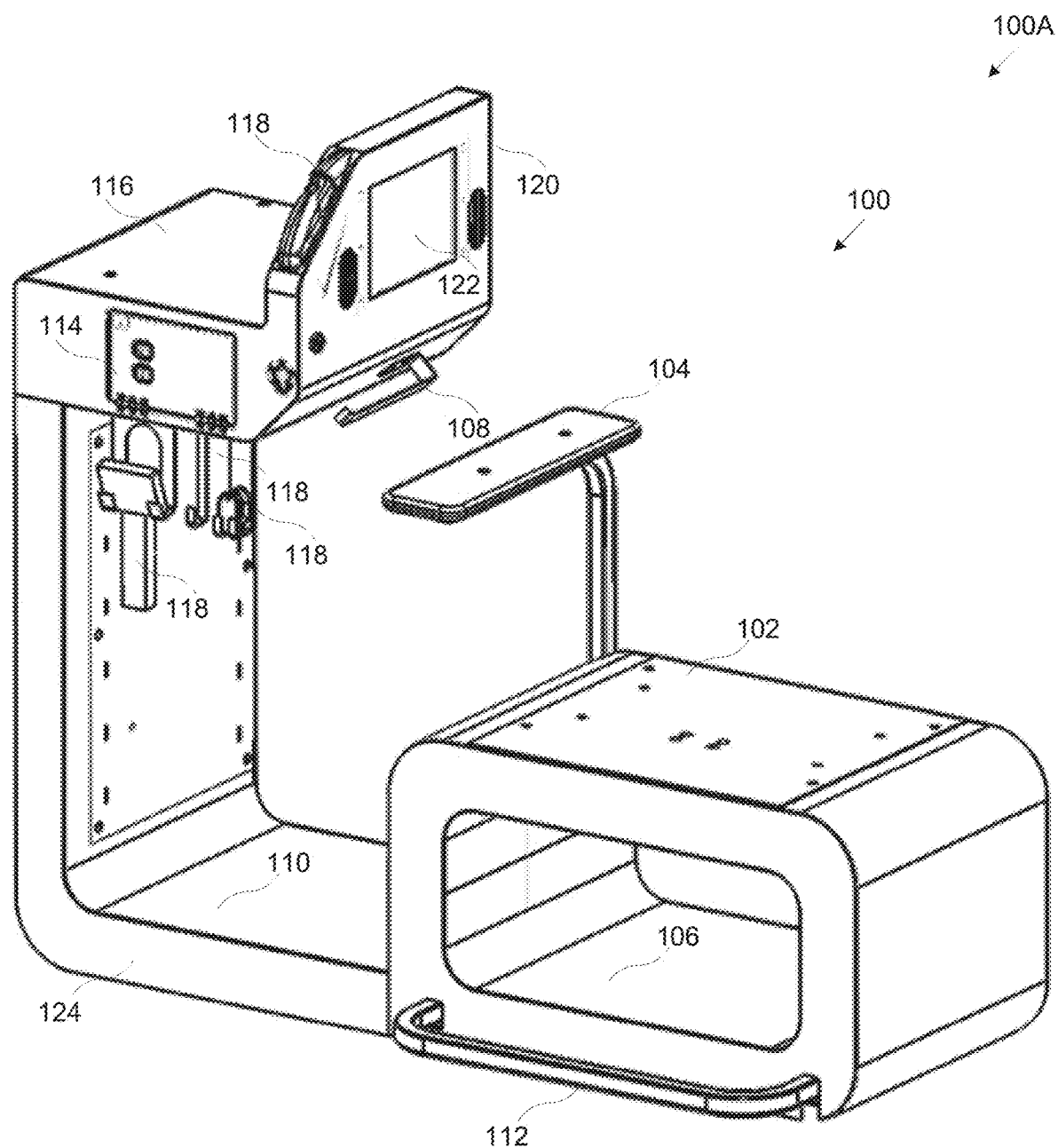
FIG 1A: EXEMPLARY KIOSK, PERSPECTIVE VIEW

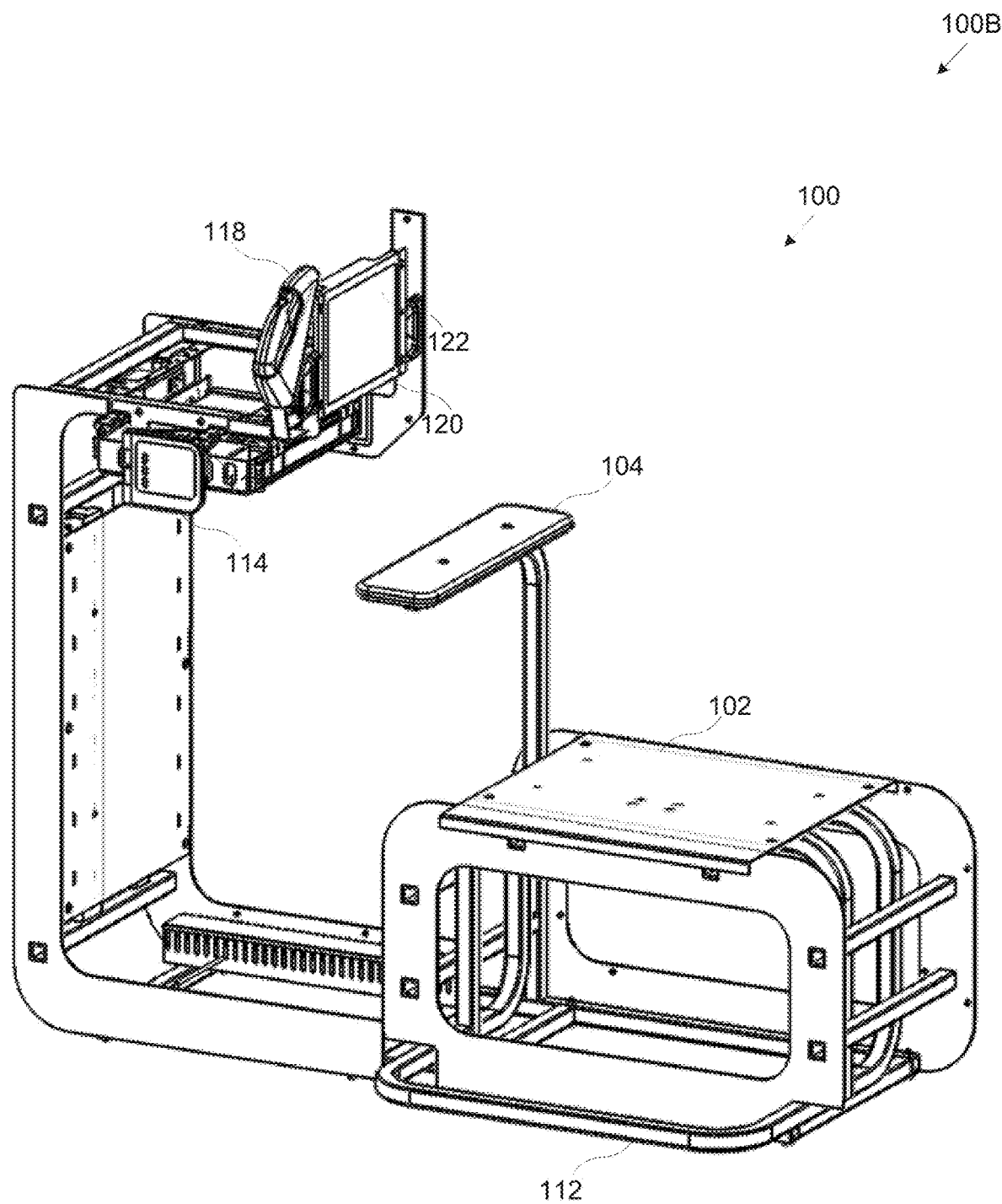
FIG 1B: EXEMPLARY KIOSK, PERSPECTIVE VIEW WITH EXTERIOR HOUSING REMOVED

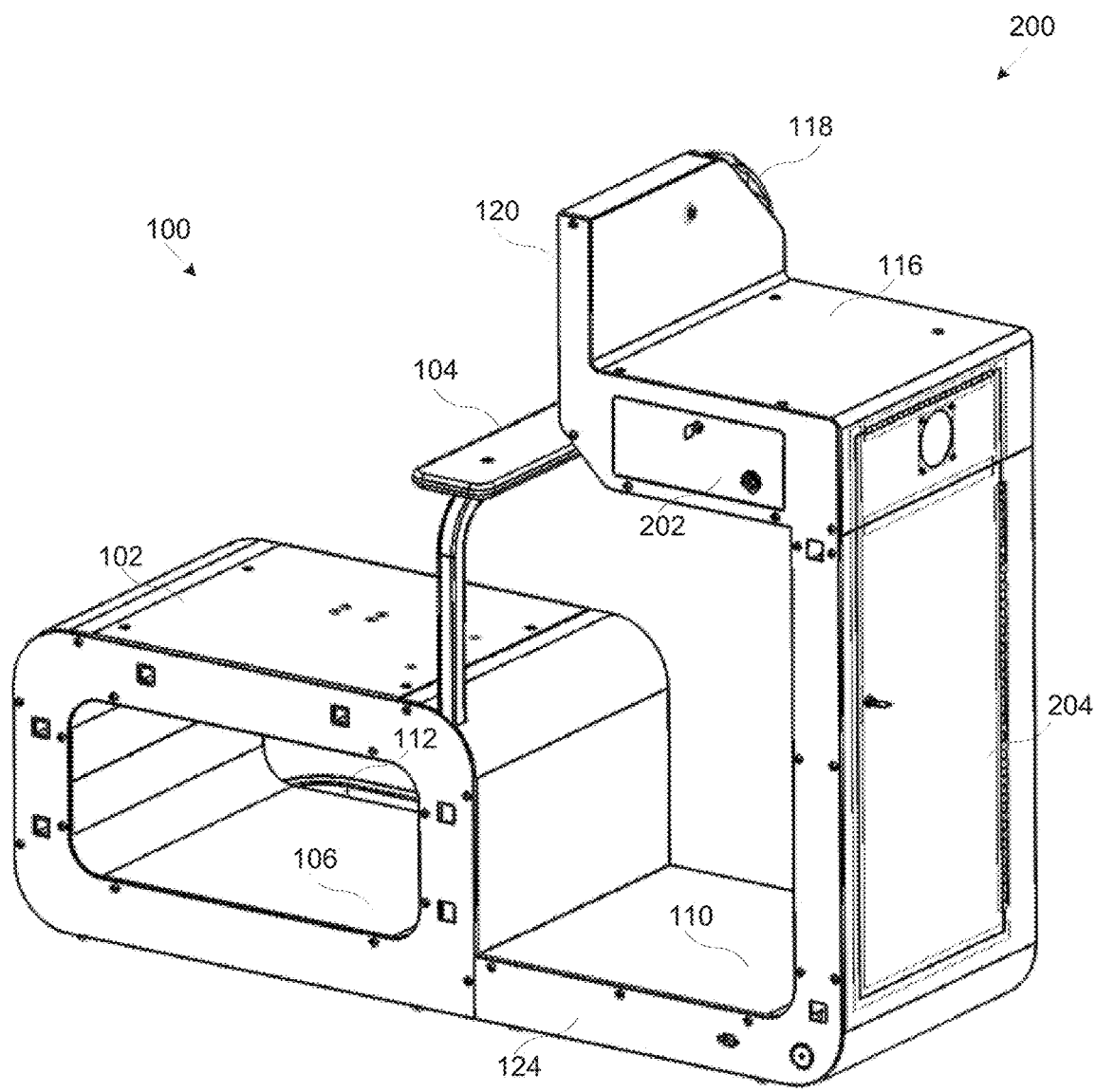
FIG 2: EXEMPLARY KIOSK, ALTERNATIVE PERSPECTIVE VIEW

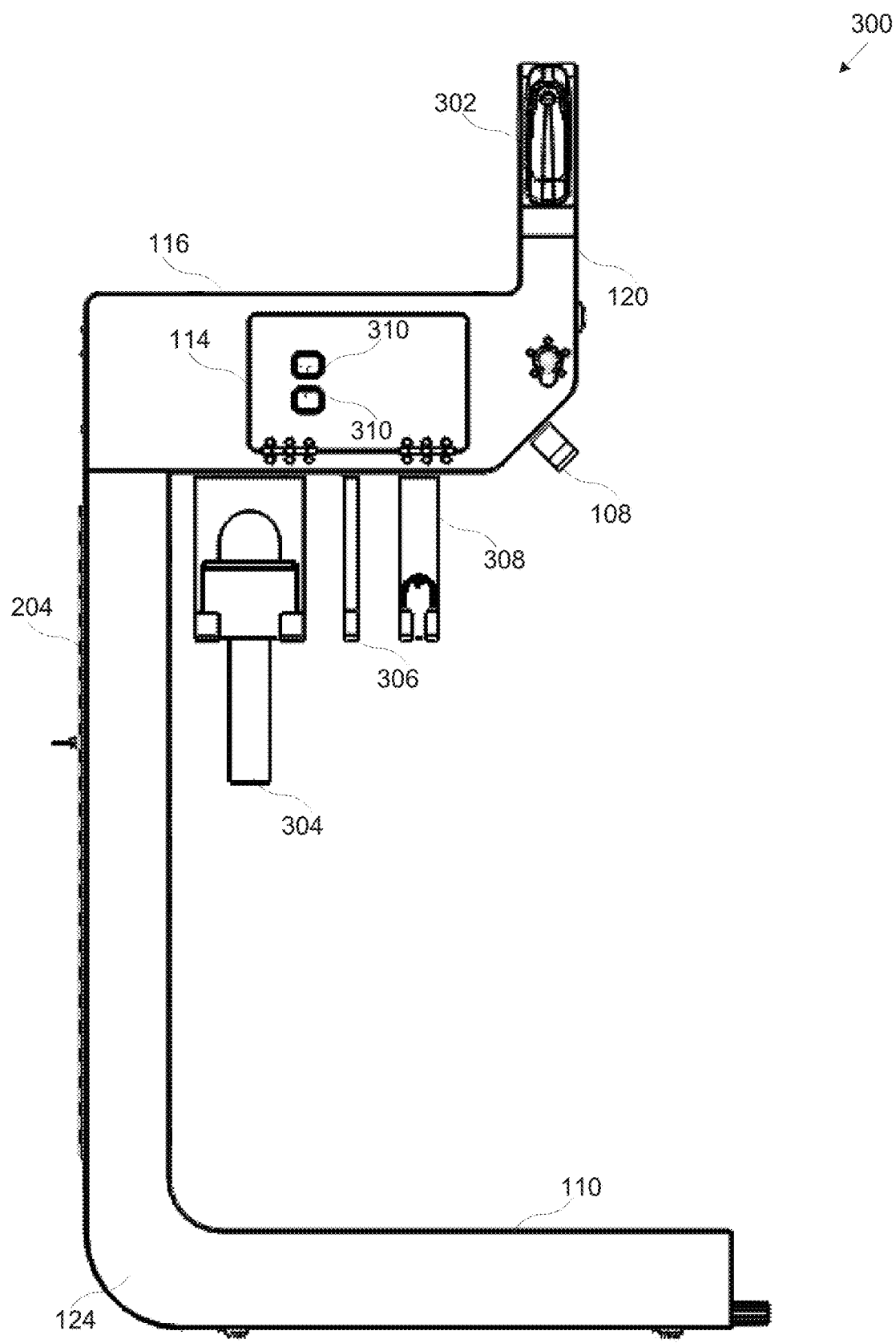
FIG 3: EXEMPLARY KIOSK, SIDE VIEW

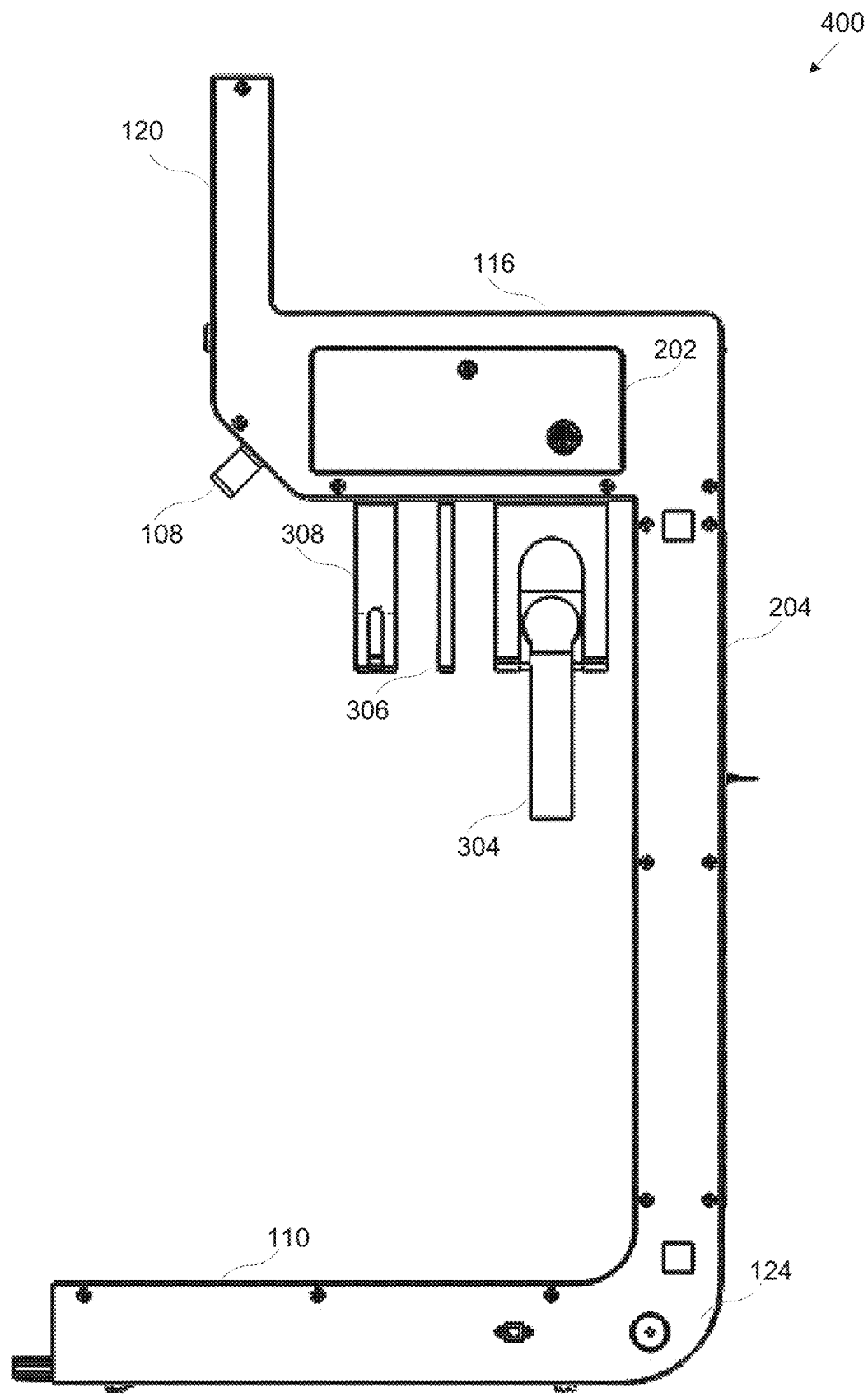
FIG 4: EXEMPLARY KIOSK, ALTERNATIVE SIDE VIEW

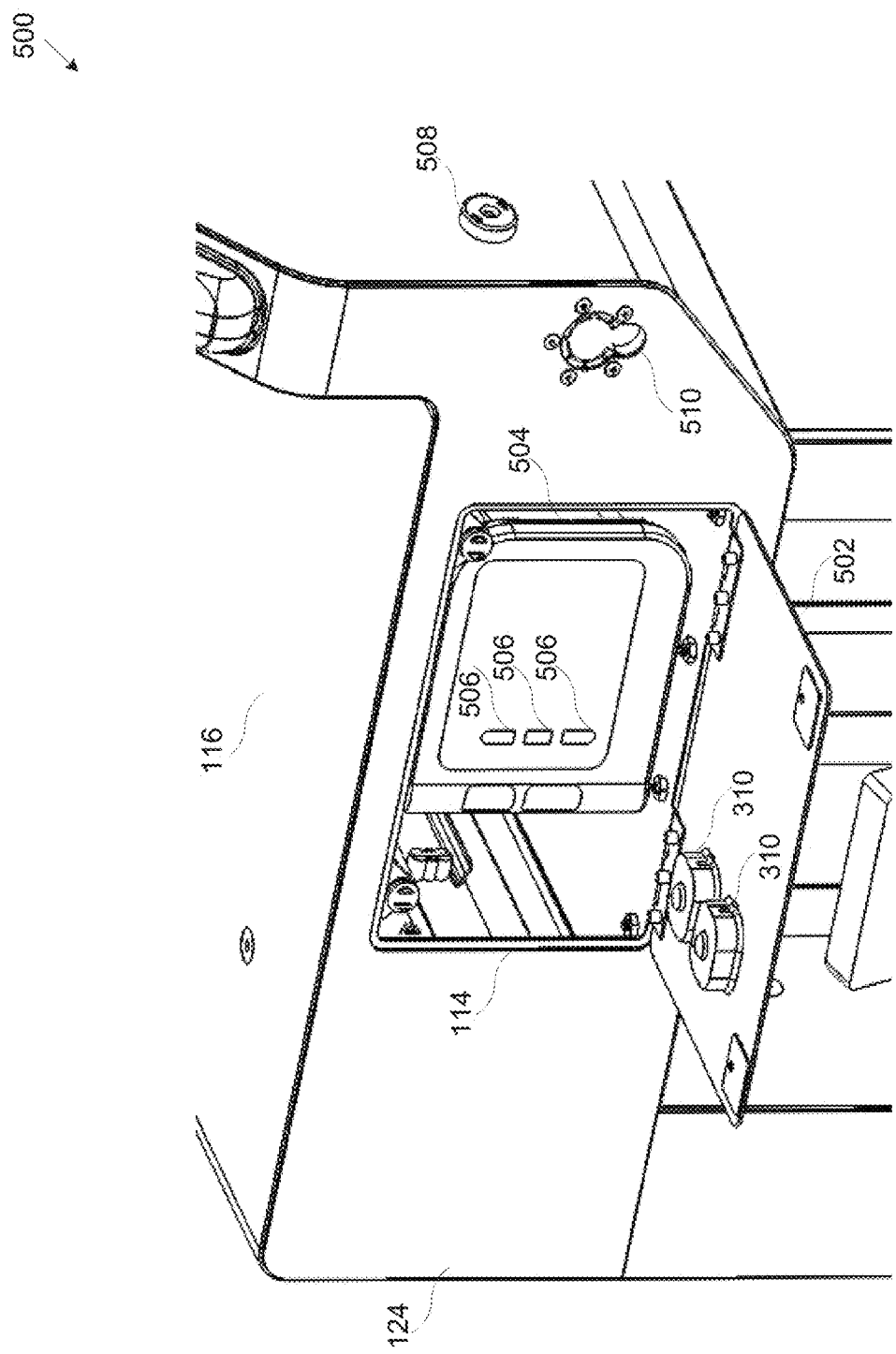
FIG 5: EXEMPLARY COMPARTMENT OF KIOSK

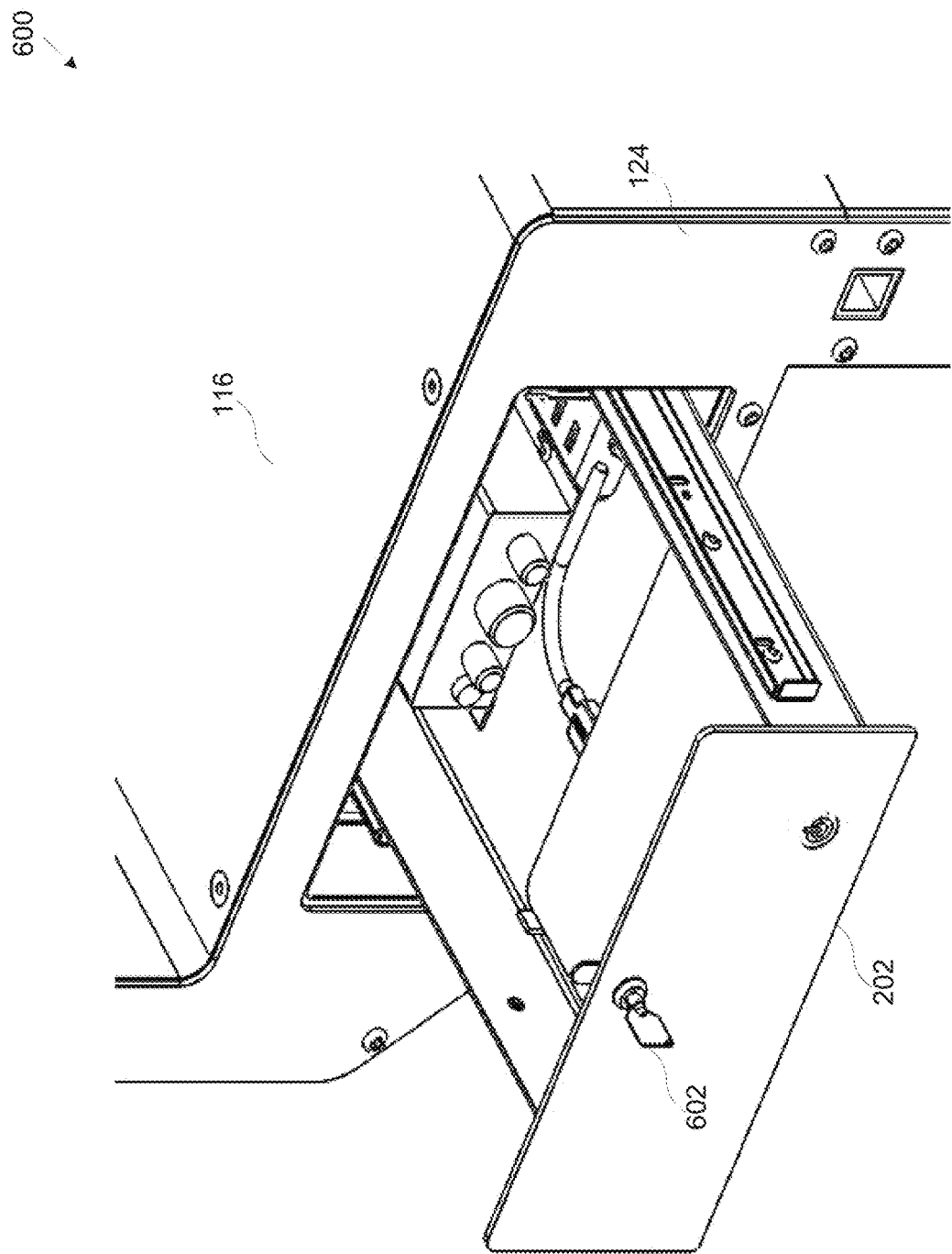
FIG 6: EXEMPLARY DRAWER OF KIOSK

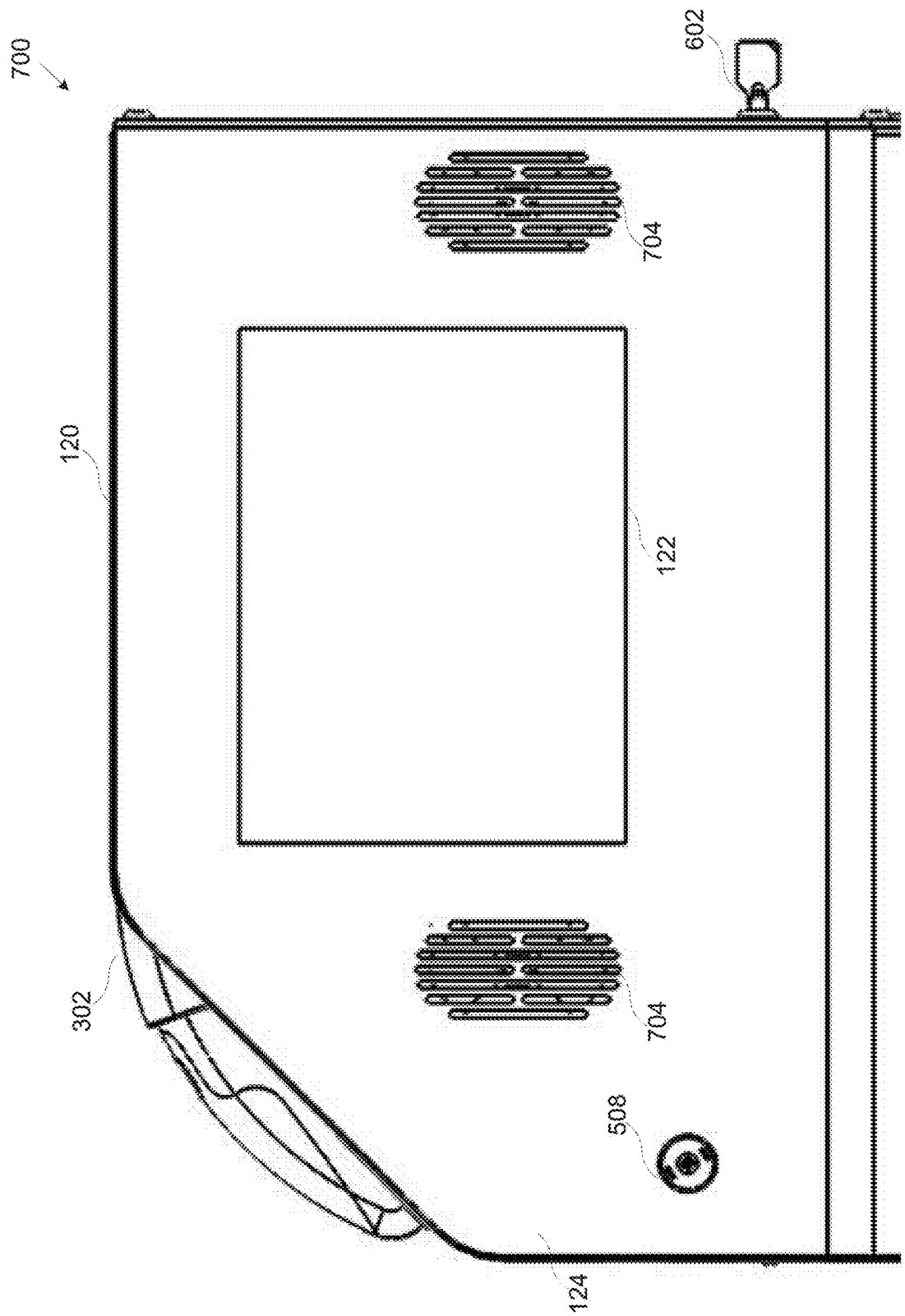
FIG 7: EXEMPLARY TARGETED-CONTENT DISPLAY DEVICE

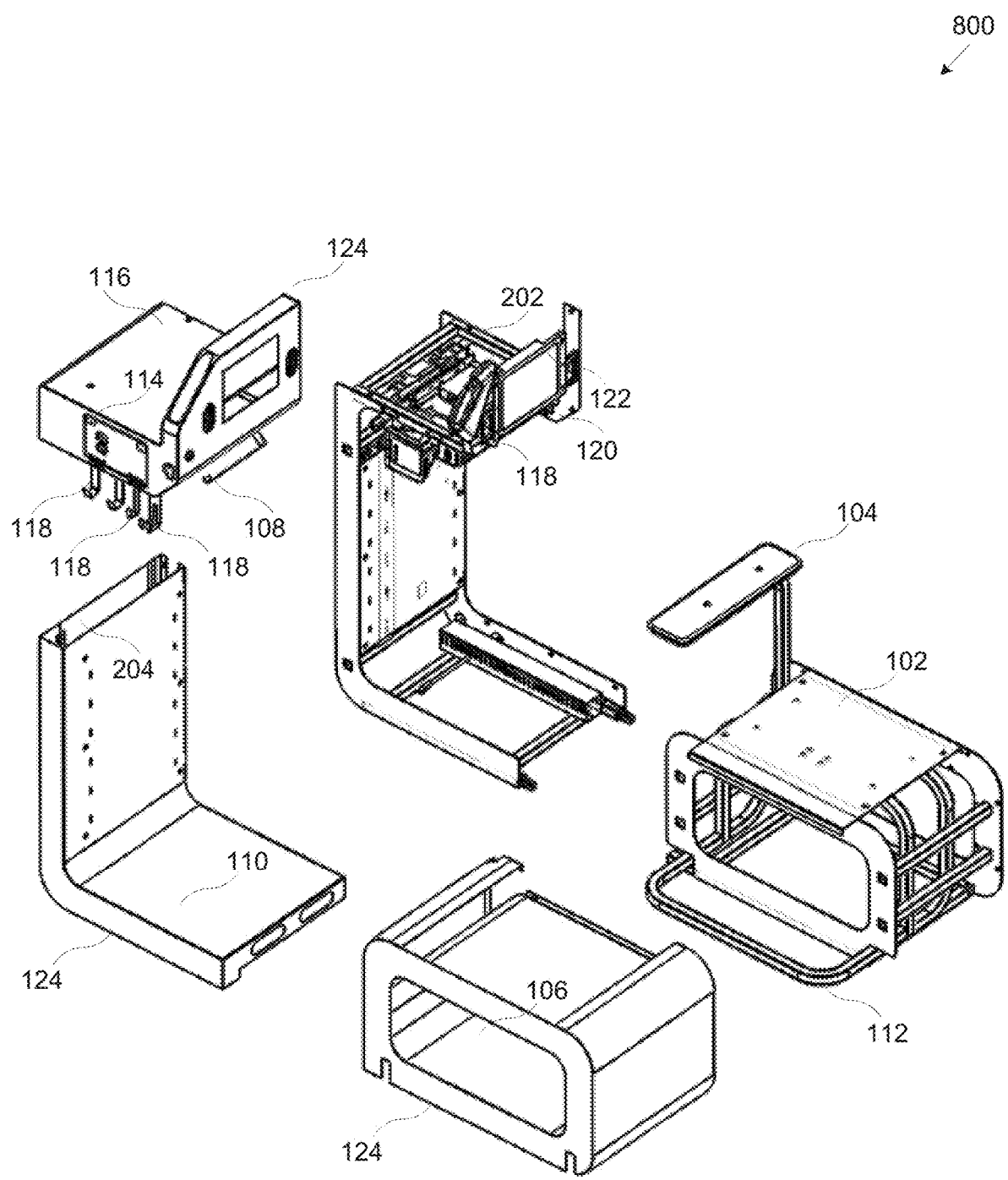
FIG 8: EXEMPLARY KIOSK, EXPLODED VIEW

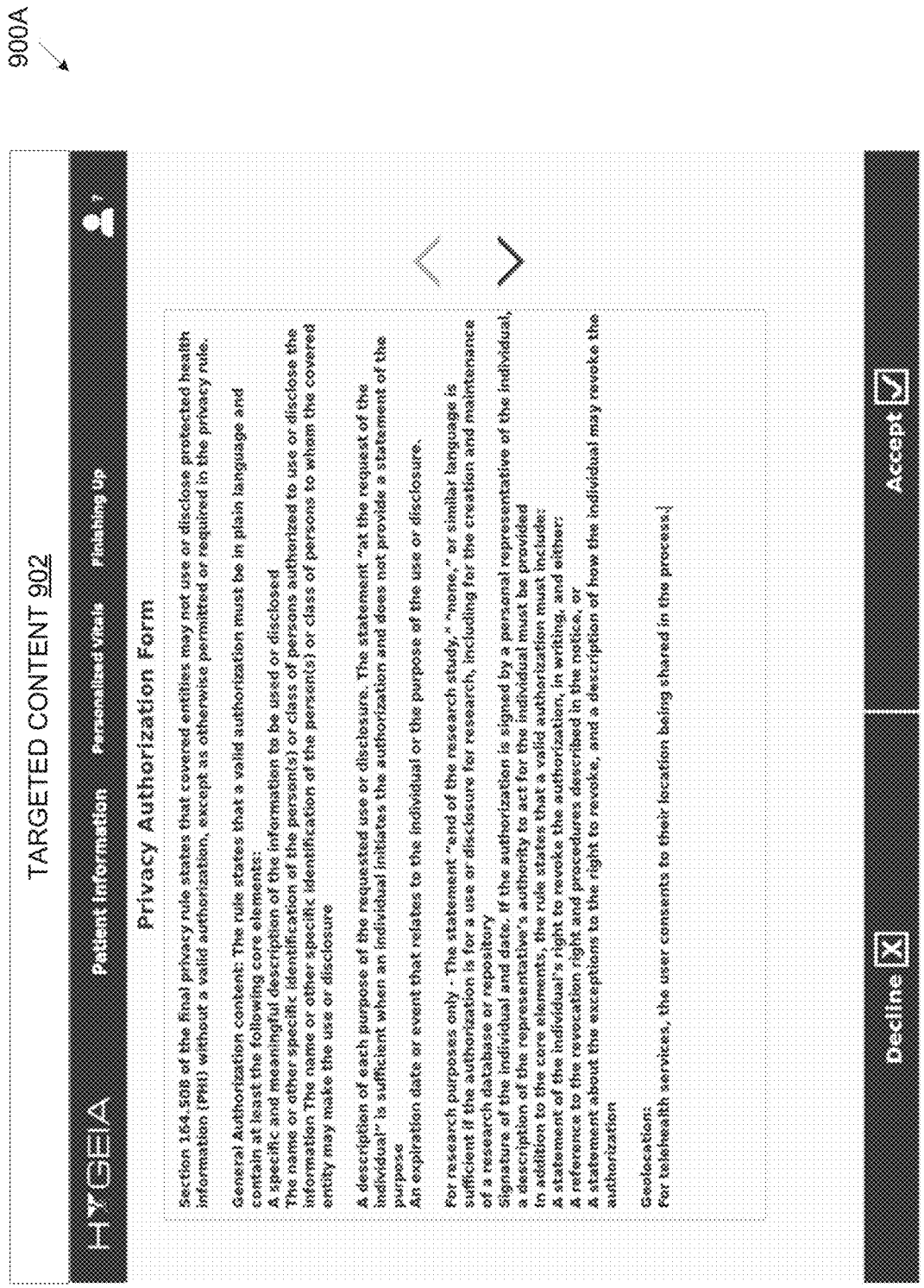
FIG 9A: EXEMPLARY TARGETED-CONTENT DISPLAY DEVICE SCREENSHOT

FIG 9B: EXEMPLARY TARGETED-CONTENT DISPLAY DEVICE SCREENSHOT

900C

HYGEIA

Patient Information Health Concerns Personalized Visit Health History Health Insurance John S What is the main problem?
Chest Pain How painful is the problem?
5 (painful)

How long has the problem occured?
1 month

Does it occur at a certain time?
No

If yes, when?

Back

TARGETED CONTENT 906

*FIG 9C: EXEMPLARY TARGETED-CONTENT DISPLAY DEVICE SCREENSHOT*

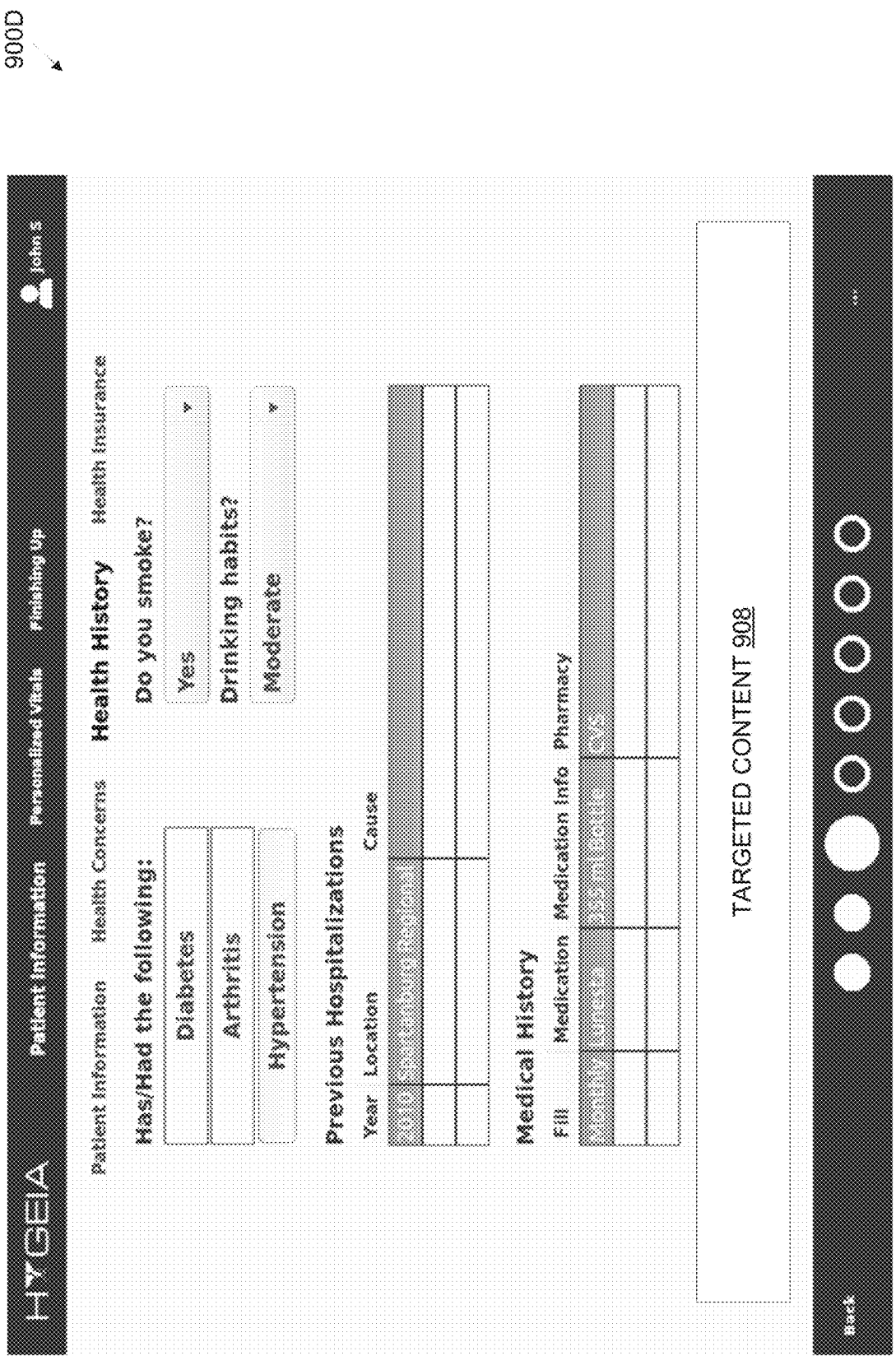
FIG 9D: EXEMPLARY TARGETED-CONTENT DISPLAY DEVICE SCREENSHOT

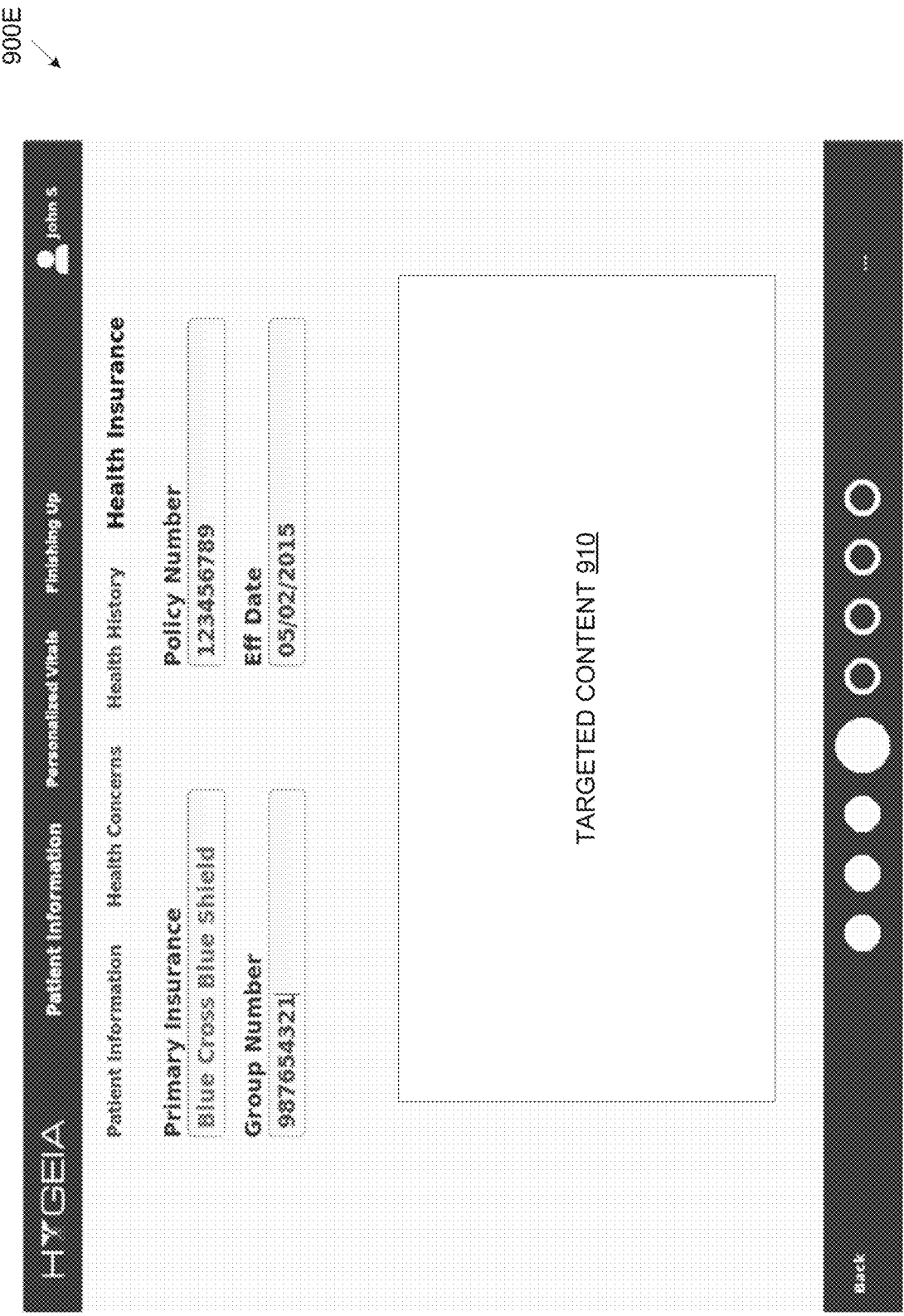
FIG 9E: EXEMPLARY TARGETED-CONTENT DISPLAY DEVICE SCREENSHOT

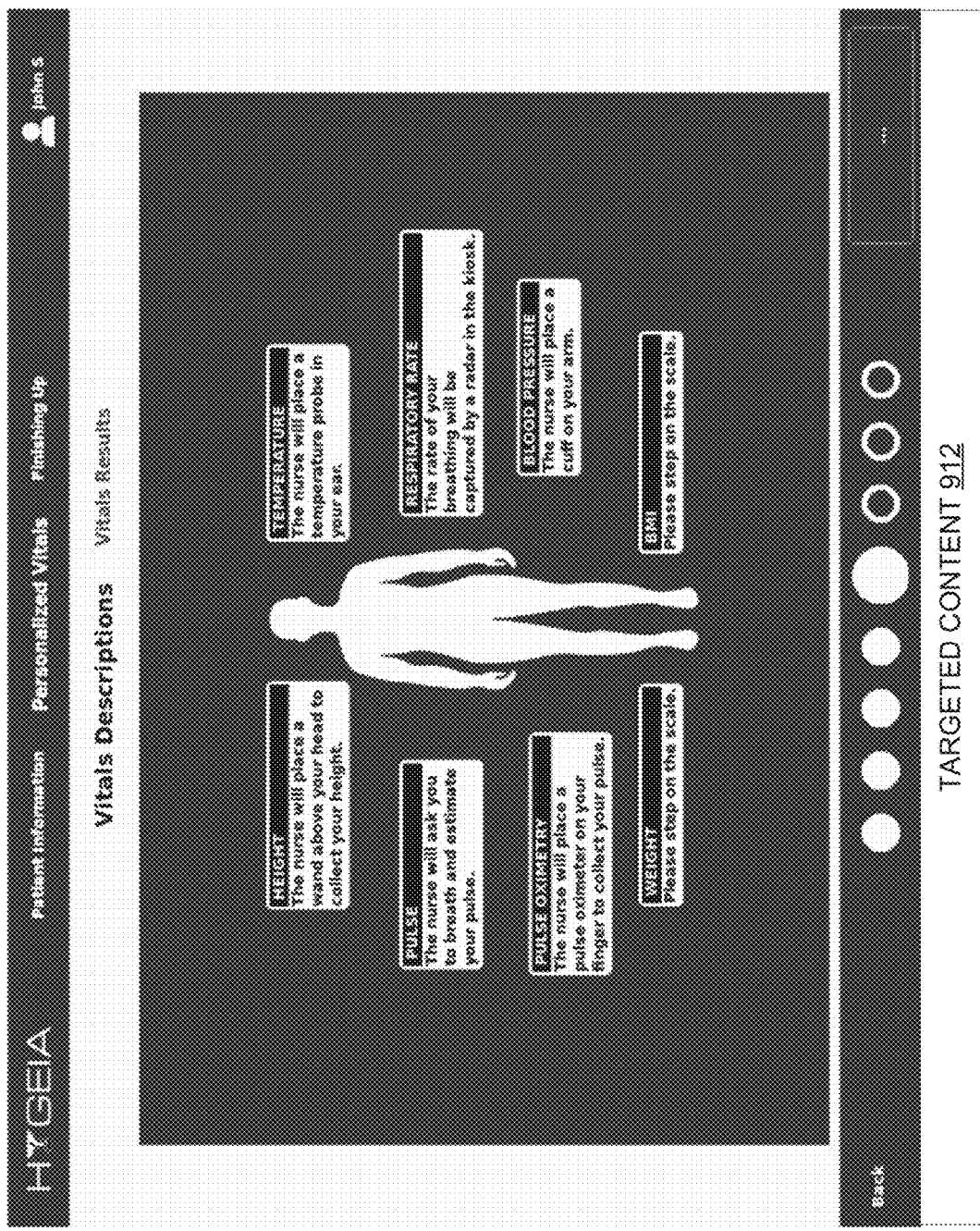
FIG 9F: EXEMPLARY TARGETED-CONTENT DISPLAY DEVICE SCREENSHOT

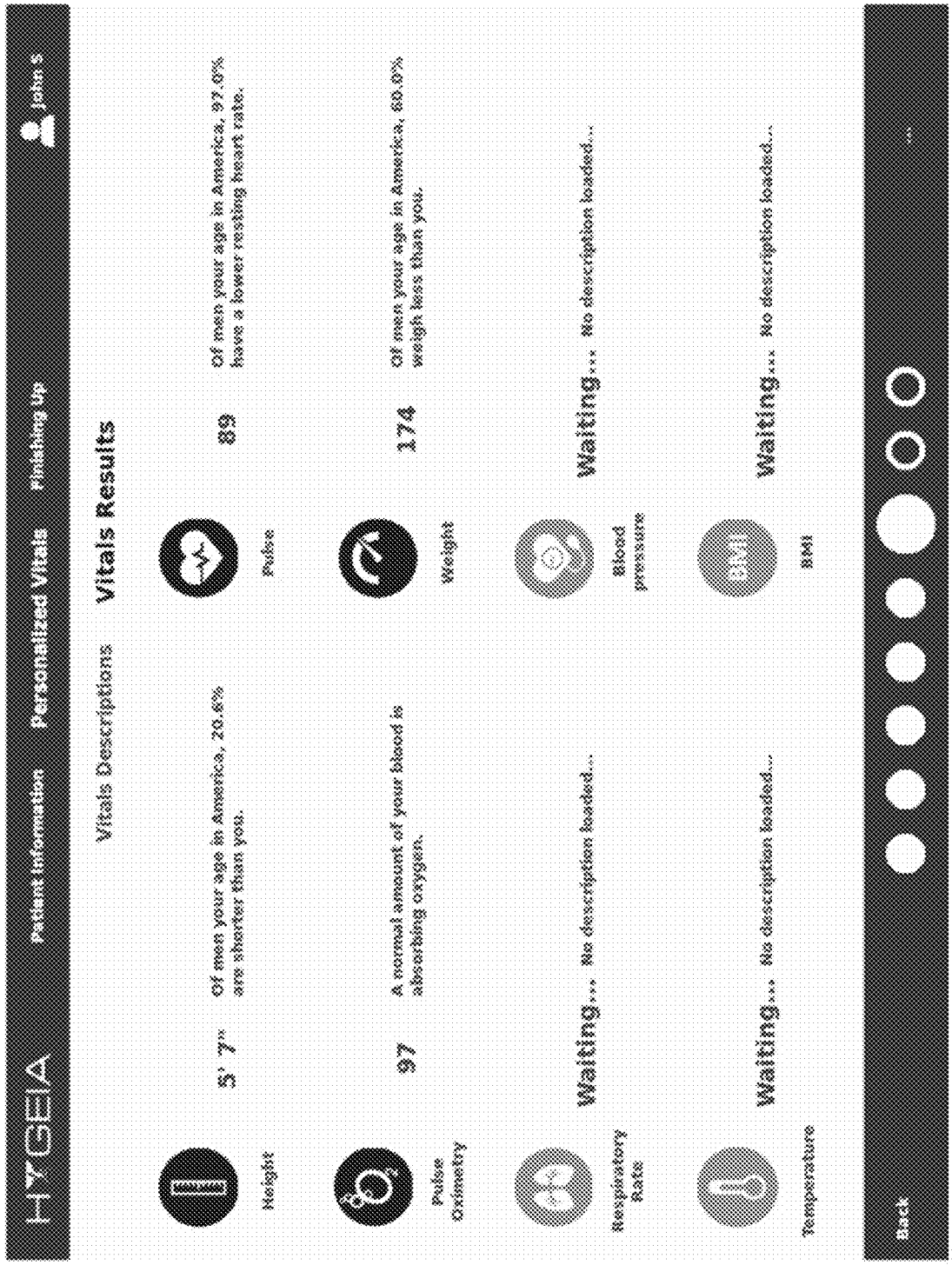
FIG 9G: EXEMPLARY TARGETED-CONTENT DISPLAY DEVICE SCREENSHOT

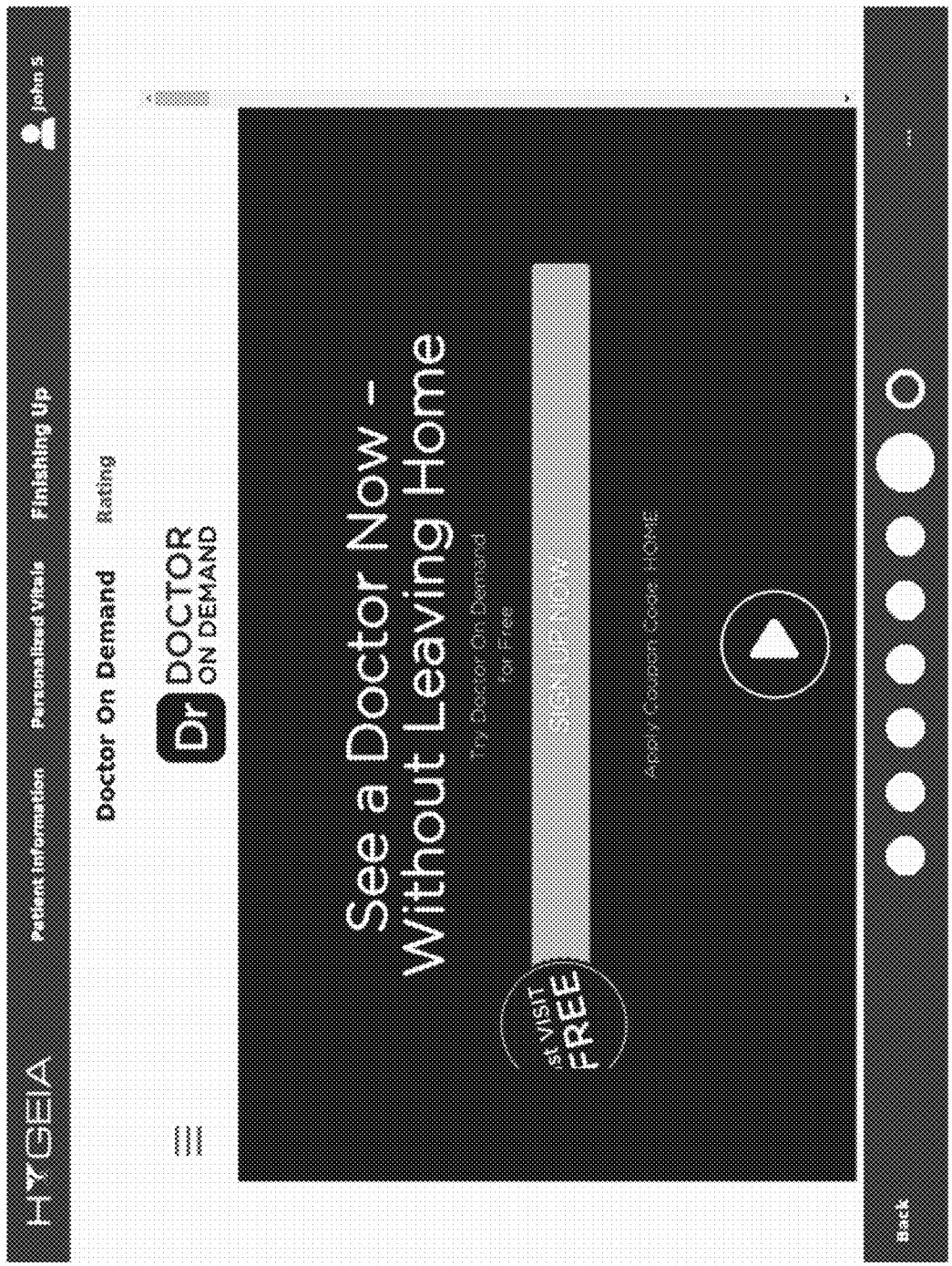
FIG 9H: EXEMPLARY TARGETED-CONTENT DISPLAY DEVICE SCREENSHOT

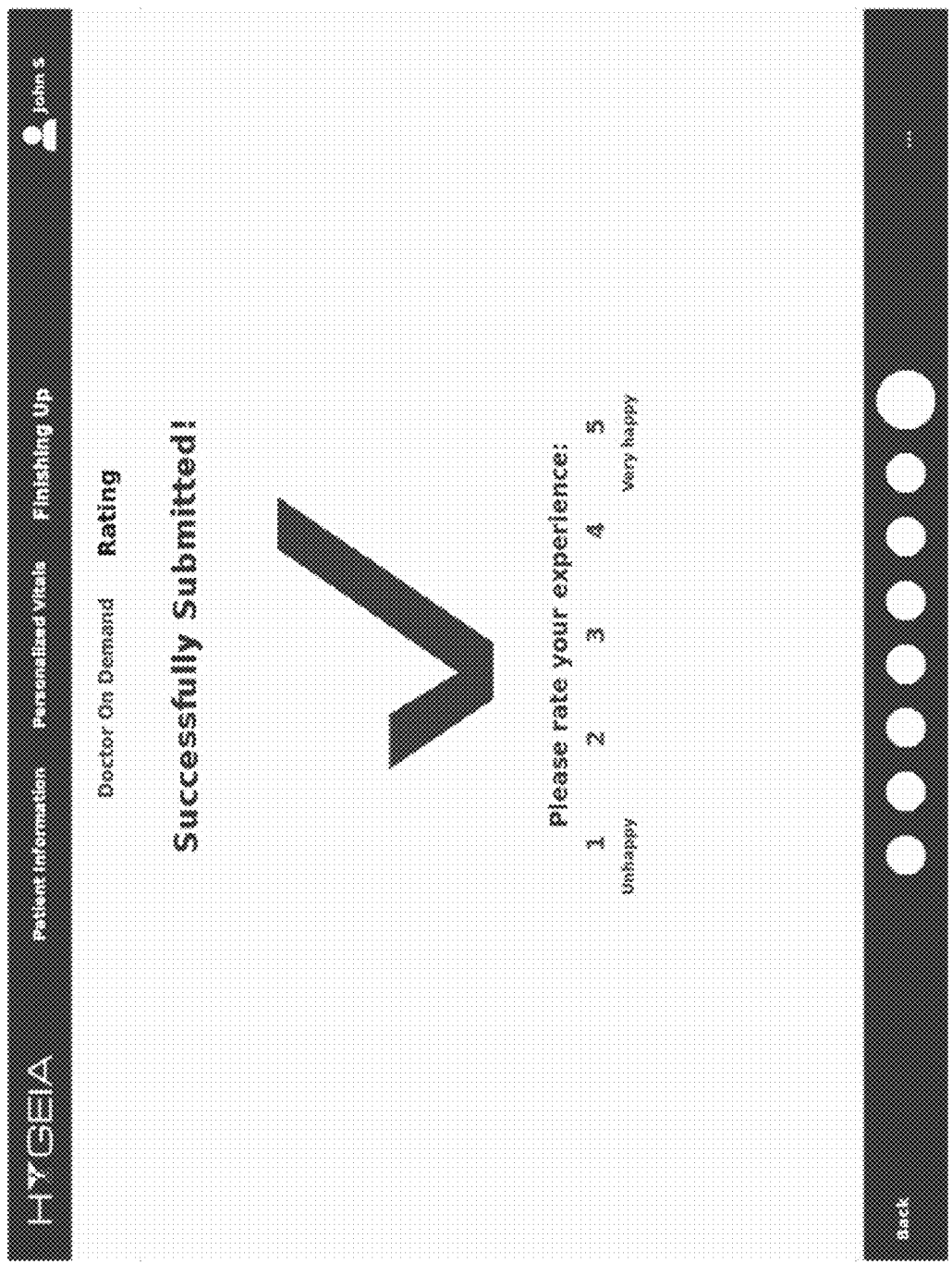
FIG 9I: EXEMPLARY TARGETED-CONTENT DISPLAY DEVICE SCREENSHOT

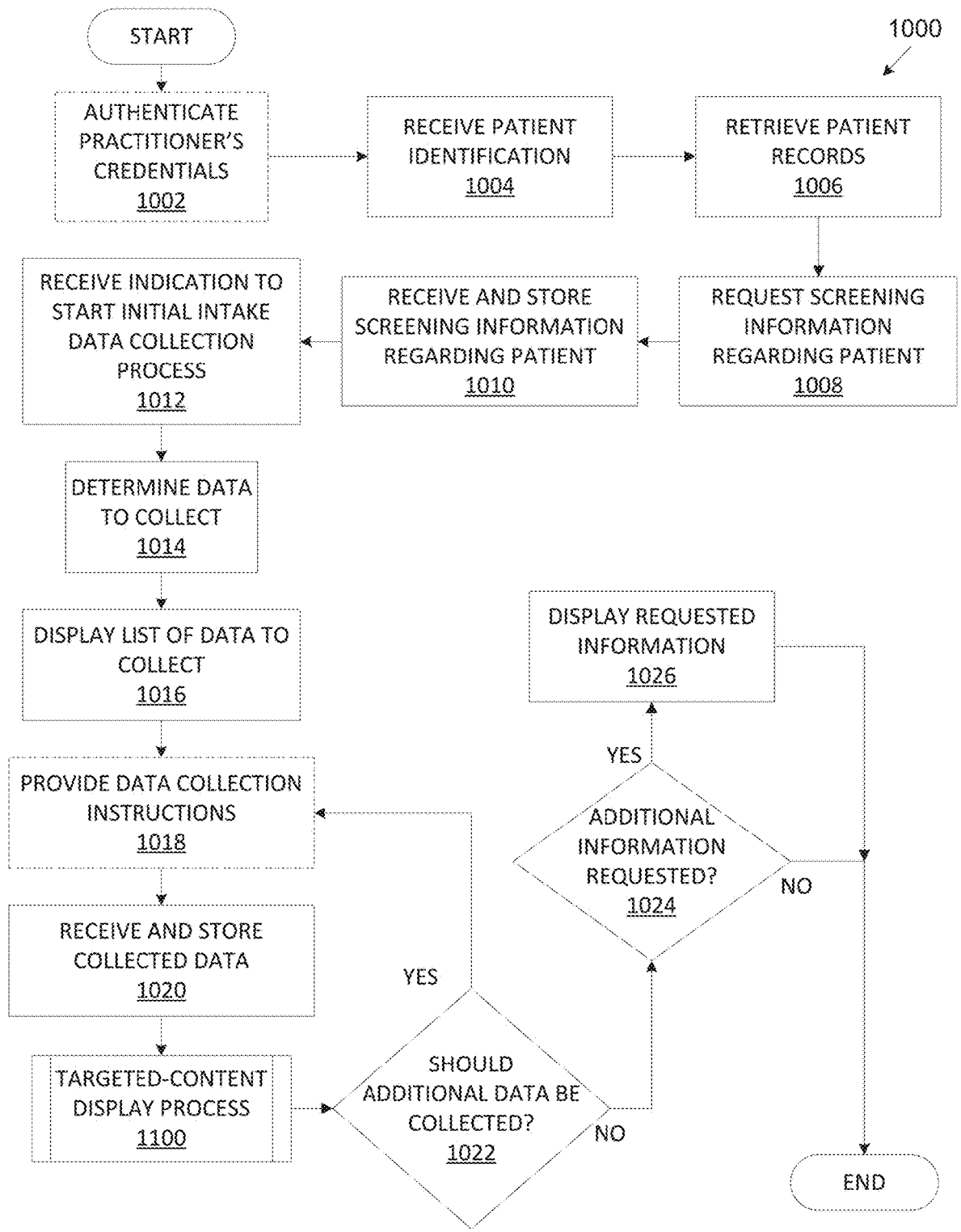
FIG 10: EXEMPLARY PHYSIOLOGICAL DATA COLLECTION PROCESS

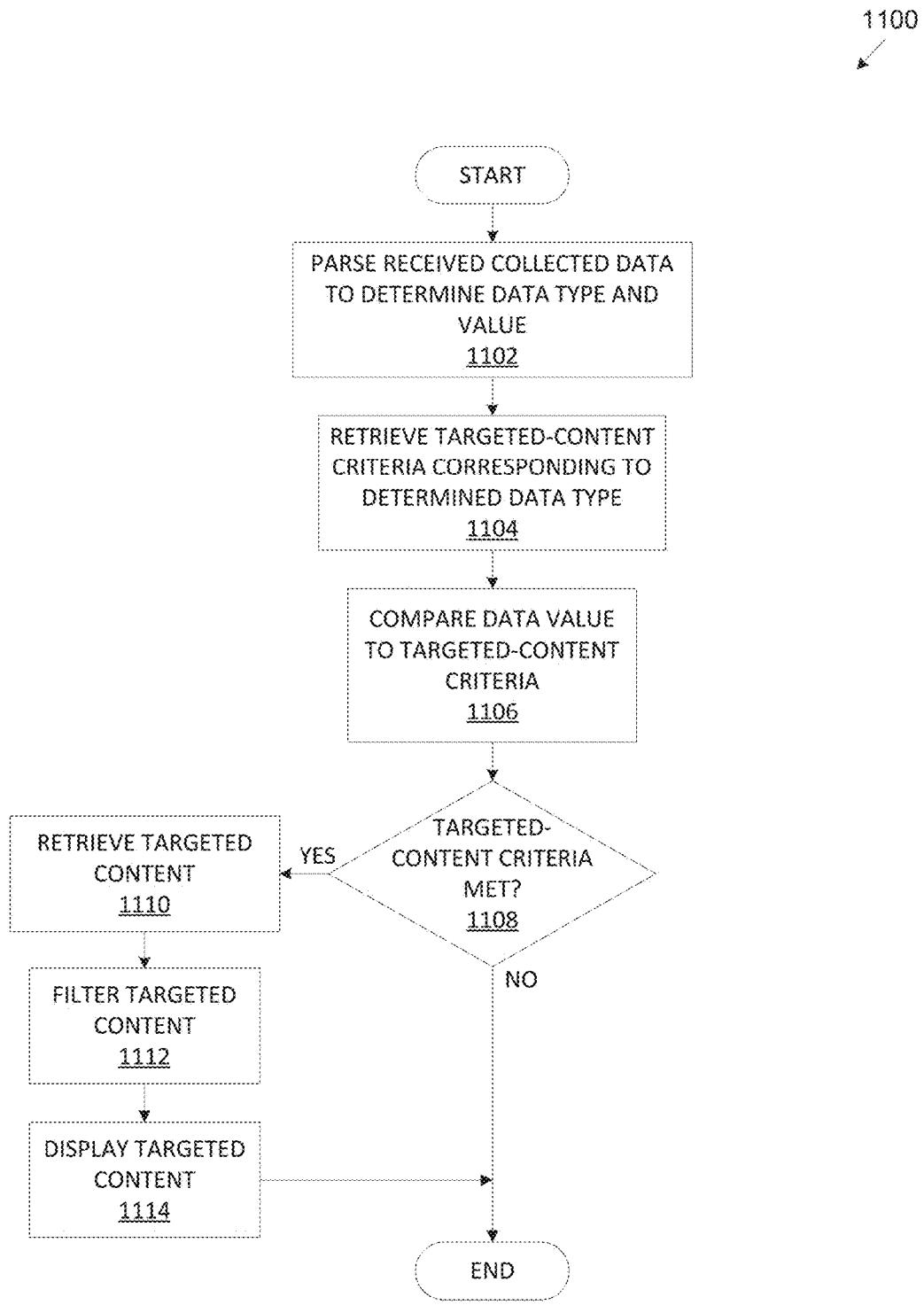
FIG 11: EXEMPLARY TARGETED-CONTENT DISPLAY PROCESS

SYSTEMS, APPARATUSES, AND METHODS FOR PHYSIOLOGICAL DATA COLLECTION AND PROVIDING TARGETED CONTENT

CROSS REFERENCE TO RELATED APPLICATIONS

This application is a divisional of, and claims the benefit of and priority under 35 U.S.C. 120 to U.S. Non-Provisional patent application Ser. No. 14/925,138, filed Oct. 28, 2015, and entitled "Systems, Apparatuses, and Methods for Physiological Data Collection and Providing Targeted Content," and claims benefit under 35 U.S.C. § 119(e) of U.S. Provisional Patent Application No. 62/069,550, filed Oct. 28, 2014, and entitled "Systems, Apparatuses, and Methods Relating to Healthcare and Medical Kiosks and Methodology for Real Time Updating of Point of Contact Targeted Advertising on Same." Additionally, this application claims priority to and incorporates by reference herein in its entirety U.S. Design patent application Ser. No. 29/505,330, filed Sep. 17, 2015, and entitled "Hygeia Health Station."

TECHNICAL FIELD

The present systems, apparatuses, and methods relate generally to physiological data collection, and more particularly to kiosks that permit the collection of multiple types of physiological, physical, biometric, or other healthcare-related data (e.g., height, weight, temperature, blood pressure, etc.) from a patient and provide targeted content to the patient based, at least in part, on the collected data.

BACKGROUND

Prior to seeing a doctor (but generally while at a doctor's office), a patient must first undergo initial physiological data collection (e.g., height, weight, temperature, blood pressure, current symptoms, allergies, health history, etc.) as part of the intake process. In some offices, the devices that collect much of this data are limited in number and must be transported to each patient room prior to use (or patients must travel to different rooms to use the devices). Similarly, after collecting the data, the nurse or other medical professional must manually input the data into the patient's chart or electronic medical record. These limitations cause inefficiencies in the intake process that increase patient wait times, reduce medical professional efficiency, and increase risk of mistranslation of collected data. Additionally, there is no opportunity during this intake process to provide targeted advertising to the patient and/or collect revenue from the patient. Similarly, it is difficult to conduct this process as part of a telehealth (e.g., remote diagnostics, etc.) session.

Therefore, there is a long-felt but unresolved need for a system, apparatus, or method that permits the collection of multiple types of physiological data from a patient and provides targeted content to the patient based on the collected data.

BRIEF SUMMARY OF THE DISCLOSURE

Briefly described, and according to one embodiment, aspects of the present disclosure generally relate to systems, apparatuses (e.g., kiosks, terminals, stations, booths, etc.), and methods that permit the collection of multiple types of physiological data from a patient and provide targeted content to the patient based, at least in part, on the collected data.

In one embodiment, the kiosk (alternatively referred to herein as a "terminal," "station," "booth," etc.) comprises various ergonomic features such as one or more foot rests, arm rests, seats, storage compartments, etc. so that the patient may comfortably use the kiosk during the collection of physiological data (e.g., taking of vital signs such as heart rate, temperature, etc.). Similarly, the kiosk comprises various compartments and locations to hold the various physiological data collection devices (e.g., thermometers, pulse oximeters, sphygmomanometers, stethoscopes, etc.), auxiliary supplies (e.g., bandages, tongue depressors, cotton swabs, alcohol wipes, batteries, cables, etc.), and electronic computing devices (e.g., laptops, tablets, etc.) that are used during the physiological data collection process. Finally, the kiosk comprises a targeted-content display devices (e.g., one or more screens, audio speakers, processors, databases, etc.) that displays targeted content (e.g., advertisements specifically tailored to the patient based on the collected physiological data and/or other content such as articles, news, informational flyers, etc.) to the patient during the data collection process based on the collected physiological data.

Generally, the kiosk permits a medical professional (e.g., nurse, technician, doctor, etc.) or a patient to efficiently collect multiple types of physiological data regarding the patient in one location and input that collected data into the patient's medical record while the patient views targeted content generated based, at least in part, on the collected physiological data, the patient's medical history, the reason for the patient's visit, etc. For example, when a patient arrives in a doctor's office for an appointment, the patient's physiological data (e.g., vital signs, temperature, blood pressure, heart rate, weight, height, etc.) is initially collected at the kiosk and recorded in the patient's medical record as part of the intake process (e.g., directly from the physiological data collection devices, manually by the medical professional, etc.). During this intake process, the patient is able to view and interact with targeted content corresponding to the physiological data that is being collected (e.g., if the patient has high blood pressure, then the patient may be shown targeted content for a medicine the lowers blood pressure; if the patient has a low resting heart rate, then the patient may be shown targeted content for exercise equipment; etc.). This targeted content may be displayed based on certain criteria (e.g., ranges, thresholds, rules, etc.) that are established by the advertiser, the medical professional, etc.

In one embodiment, an apparatus for collecting physiological data relating to a user, comprising: a generally L-shaped housing having a first lower end and a second upper end, wherein the first lower end of the housing comprises a raised seat on which a user sits while physiological data relating to the user is collected; a substantially horizontal platform resting on the second upper end of the generally L-shaped housing, the platform housing electrical components operatively connected to a plurality of data collection devices, wherein the plurality of data collection devices are physically positioned on the exterior of the platform to enable interaction with the user; and a display device extending substantially vertically from the platform for displaying content to the user.

In one embodiment, an apparatus, comprising: a base; a display device connected to the base; a processor operatively connected to the display device; and two or more devices capable of collecting physiological data relating to a patient, wherein the collected physiological data is processed by the processor after collection by the two or more devices.

In one embodiment, a method, comprising the steps of: receiving, at an electronic computing device, physiological data relating to a patient, wherein the physiological data is measured from the patient by the electronic computing device; retrieving, from a system database, one or more targeted-content criteria corresponding to the received physiological data; comparing the received physiological data to the one or more retrieved targeted-content criteria; determining, based on the comparison, one or more targeted-content items to display via the electronic computing device to the patient; and displaying, via the electronic computing device, electronic data corresponding to the one or more targeted-content items to the patient.

According to one aspect of the present disclosure, the apparatus, further comprising an armrest that comprises a first portion that extends approximately perpendicular from the raised seat and a second portion that extends approximately perpendicular from the first portion and substantially parallel to the raised seat, which facilitates the collection of the physiological data. Furthermore, the apparatus, wherein the raised seat is substantially rectangular and the top surface of the substantially rectangular raised seat further comprises a device that collects data corresponding to the mass of the user. Moreover, the apparatus, wherein the platform further comprises a compartment for storing a device that collects data corresponding to the blood pressure of the user and permits operation of the device during collection of the data without opening the compartment. Further, the apparatus, wherein the platform further comprises a dispenser that dispenses single-use medical supplies for use while the physiological data is collected. Additionally, the apparatus, wherein the display device further comprises a substantially-triangular cutout from a corner of the display device and the corner comprises a receptacle to store a thermometer. Also, the apparatus, wherein the plurality of data collection devices comprise a thermometer, a pulse oximeter, a sphygmomanometer, a stethoscope, a digital otoscope, and a digital dermascope.

According to one aspect of the present disclosure, the apparatus, wherein the base further comprises a device that collects data corresponding to the mass of the patient. Furthermore, the apparatus, wherein the display device is operative to: receive, from the processor, electronic data corresponding to the collected physiological data; retrieve, from a system database, one or more targeted-content criteria corresponding to the received physiological data; compare the received physiological data to the one or more retrieved targeted-content criteria; determine, based on the comparison, one or more targeted-content items to display to the patient; and display electronic data corresponding to the one or more retrieved targeted-content items to the patient. Moreover, the apparatus, wherein the display device is further operative to: receive user engagement with the one or more displayed targeted-content items; and based on the user engagement, initiate a predetermined action, wherein the predetermined action comprises one or more of the following: retrieve, from the system database, additional information corresponding to the one or more displayed targeted-content items and display the retrieved additional information to the patient; request, from a third party system, additional information corresponding to the one or more displayed targeted-content items; receive, from the third party system, the requested additional information corresponding to the one or more displayed targeted-content items; and display the received additional information to the patient; and transmit to a third party system a request for additional information corresponding to the one or more displayed targeted-content items, wherein the request for additional information comprises correspondence information for the patient. Further, the apparatus, wherein the targeted-content criteria comprises a range in which the received physiological data may fall, the one or more targeted-content items comprise a first one or more targeted-content items corresponding to one or more pharmaceutical products that treat one or more conditions that cause the received physiological data to fall within the range, displaying the first one or more retrieved targeted-content items to the patient occurs only when the received physiological data falls within the range, and the display device is further operative to: determine, based on the comparison, a second one or more targeted-content items to display to the patient; retrieve, from the system database, the second one or more targeted-content items for display to the patient; and display the second one or more retrieved targeted-content items to the patient, wherein displaying the second one or more retrieved targeted-content items to the patient occurs only when the received physiological data falls outside the range.

According to one aspect of the present disclosure, the method, further comprising the steps of: receiving, at the electronic computing device, user engagement with the one or more displayed targeted-content items; and based on the user engagement, initiating a predetermined action via the electronic computing device. Additionally, the method, wherein the predetermined action comprises one or more of the following steps: retrieving, from the system database, additional information corresponding to the one or more displayed targeted-content items and displaying the retrieved additional information, via the electronic computing device, to the patient; requesting, from a third party system, additional information corresponding to the one or more displayed targeted-content items; receiving, from the third party system, the requested additional information corresponding to the one or more displayed targeted-content items; and displaying the received additional information, via the electronic computing device, to the patient; and transmitting to a third party system a request for additional information corresponding to the one or more displayed targeted-content items, wherein the request for additional information comprises correspondence information for the patient. Also, the method, wherein the targeted-content criteria comprises a range in which the received physiological data may fall and wherein displaying, via the electronic computing device, the one or more retrieved targeted-content items to the patient occurs only when the received physiological data falls within the range. Furthermore, the method, wherein the one or more targeted-content items comprise a first one or more targeted-content items, further comprising the steps of: determining, based on the comparison, a second one or more targeted-content items to display via the electronic computing device to the patient; retrieving, from the system database, the second one or more targeted-content items for display via the electronic computing device to the patient; and displaying, via the electronic computing device, the second one or more retrieved targeted-content items to the patient, wherein displaying, via the electronic computing device, the second one or more retrieved targeted-content items to the patient occurs only when the received physiological data falls outside the range. Moreover, the method, further comprising the step of collecting in real time, via a physiological data collection device, physiological data relating to the patient. Further, the method, wherein comparing the received physiological data to the one or more retrieved targeted-content criteria further comprises comparing other data relating to the patient to the one or more retrieved targeted-content criteria. Additionally, the method, wherein the one or more targeted-content items comprise advertisements.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 1 (consisting of FIGS. 1A and 1B) is a perspective view of a kiosk in accordance with one embodiment of the present disclosure.

FIG. 2 is an alternative perspective view of a kiosk in accordance with one embodiment of the present disclosure.

FIG. 3 is side view of a kiosk in accordance with one embodiment of the present disclosure.

FIG. 4 is an alternative side view of a kiosk in accordance with one embodiment of the present disclosure.

FIG. 5 is a perspective view of an open compartment of a kiosk in accordance with one embodiment of the present disclosure.

FIG. 6 is a perspective view of an open drawer of a kiosk in accordance with one embodiment of the present disclosure.

FIG. 7 is a front view of a targeted-content display device of a kiosk in accordance with one embodiment of the present disclosure.

FIG. 8 is an exploded view of a kiosk in accordance with one embodiment of the present disclosure.

FIG. 9 (consisting of FIGS. 9A, 9B, 9C, 9D, 9E, 9F, 9G, 9H, and 9I) is a screenshot of an exemplary targeted-content display device of a kiosk in accordance with one embodiment of the present disclosure.

FIG. 10 is a flowchart showing an exemplary physiological data collection process according to one embodiment of the present disclosure.

FIG. 11 is a flowchart showing an exemplary targeted-content display process according to one embodiment of the present disclosure.

DETAILED DESCRIPTION

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Aspects of the present disclosure generally relate to systems, apparatuses (e.g., kiosks, terminals, stations, booths, etc.), and methods that permit the collection of multiple types of physiological, physical, biometric, or other healthcare-related data from a patient and provide targeted content to the patient based, at least in part, on the collected data.

In one embodiment, the kiosk (alternatively referred to herein as a "terminal," "station," "booth," etc.) comprises various ergonomic features such as one or more foot rests, arm rests, seats, storage compartments, etc. so that the patient may comfortably use the kiosk during the collection of physiological data (e.g., taking of vital signs such as heart rate, temperature, etc.). Similarly, the kiosk comprises various compartments and locations to hold the various physiological data collection devices (e.g., thermometers, pulse oximeters, sphygmomanometers, stethoscopes, etc.), auxiliary supplies (e.g., bandages, tongue depressors, cotton swabs, alcohol wipes, batteries, cables, etc.), and electronic computing devices (e.g., laptops, tablets, etc.) that are used during the physiological data collection process. Finally, the kiosk comprises a targeted-content display devices (e.g., one or more screens, audio speakers, processors, databases, etc.) that displays targeted content (e.g., advertisements specifically tailored to the patient based on the collected physiological data and/or other content such as articles, news, informational flyers, etc.) to the patient during the data collection process based on the collected physiological data.

Generally, the kiosk permits a medical professional (e.g., nurse, technician, doctor, etc.) or a patient to efficiently collect multiple types of physiological data regarding the patient in one location and input that collected data into the patient's medical record while the patient views targeted content generated based, at least in part, on the collected physiological data, the patient's medical history, the reason for the patient's visit, etc. For example, when a patient arrives in a doctor's office for an appointment, the patient's physiological data (e.g., vital signs, temperature, blood pressure, heart rate, weight, height, etc.) is initially collected at the kiosk and recorded in the patient's medical record as part of the intake process (e.g., directly from the physiological data collection devices, manually by the medical professional, etc.). During this intake process, the patient is able to view and interact with targeted content corresponding to the physiological data that is being collected (e.g., if the patient has high blood pressure, then the patient may be shown targeted content for a medicine the lowers blood pressure; if the patient has a low resting heart rate, then the patient may be shown targeted content for exercise equipment; etc.). This targeted content may be displayed based on certain criteria (e.g., ranges, thresholds, rules, etc.) that are established by the advertiser, the medical professional, etc.

Exemplary Embodiments

Referring now to the figures, for the purposes of example and explanation of the fundamental processes and components of the disclosed systems, apparatuses, and methods, reference is made to FIG. 1 (consisting of FIGS. 1A and 1B), which is a perspective view of an exemplary kiosk 100, according to one embodiment of the present disclosure. As will be understood and appreciated, the exemplary kiosk 100 shown in FIG. 1 represents merely one non-limiting embodiment of the present disclosure.

FIG. 1A is a perspective view 100A of an exemplary kiosk 100, according to one embodiment of the present disclosure. FIG. 1B is a perspective view 100B of an exemplary kiosk 100 with the exterior housing 124 removed to show the interior of the exemplary kiosk 100, according to one embodiment of the present disclosure. As will be understood, although the term kiosk is used throughout this disclosure, this disclosure is not limited to kiosks and is also applicable to terminals, stations, booths, or any other device capable of performing the functionality described or suggested herein. Generally, the exemplary kiosk 100 permits a medical professional to collect multiple types of physiological data (alternatively referred to herein as "vital signs," "biometric data," etc.) regarding a patient in one physical location and input that collected data into the patient's medical record while the patient views targeted content or other tailored (or non-tailored) content generated based on the collected physiological data, the patient's medical history, the reason for the patient's visit, etc. For example, when a patient arrives in a doctor's office for an appointment, the patient's physiological data (e.g., vital signs, temperature, blood pressure, heart rate, weight, height, etc.) is initially collected at the exemplary kiosk 100 and recorded in the patient's medical record as part of the intake process. In one embodiment, the patient collects the physiological data without the assistance of a medical professional (e.g., the patient operates the apparatus in a self-operation mode). During this intake process, the patient is able to view and interact with targeted content corresponding to the physiological data that is being collected (e.g., if the patient has high blood pressure, then the patient may be shown targeted content for a medicine the lowers blood pressure; if the patient has a low resting heart rate, then the patient may be shown targeted content for exercise equipment; etc.).

Accordingly, in various embodiments, the exemplary kiosk 100 comprises a seat 102, an arm rest 104, one or more storage/resting locations 106 and 108 to place the patient's personal belongings, and one or more foot rests 110 and 112 to accommodate a patient during the physiological data collection process. In one embodiment, the seat 102, arm rest 104, one or more storage/resting locations 106 and 108 to place the patient's personal belongings, and one or more foot rests 110 and 112 are adjustable to accommodate patients of different ages, genders, sizes, etc. Generally, the seat 102 provides a place for the patient to sit during the intake process. In one embodiment, the seat 102 may comprise a scale or other physiological data collection device that collects the patient's mass, weight, etc. As will be understood by one having ordinary skill in the art, the arm rest 104 permits the patient to easily sit on the seat 102 and stand up from the seated position, facilitates the capture of a patient's blood pressure in accordance with American Medical Association guidelines, and facilitates blood draws from the patient. Similarly, the one or more storage/resting locations 106 and 108 to place the patient's personal belongings permit the patient to remove and safely store items from their pockets, coats, purses, etc. so that those items do not interfere with the physiological data collection process (e.g., by increasing the patient's weight, etc.). In one embodiment, the blood pressure cuff may hang from storage/resting location 108. Finally, the one or more foot rests 110 and 112 are designed to allow patients of varying heights to sit comfortably within the kiosk 100. In one embodiment, foot rest 112 may comprise a scale that slides out from the kiosk to collect the patient's mass.

Still referring to FIG. 1, in various embodiments, the exemplary kiosk 100 comprises a compartment 114, a resting surface 116 (e.g., for resting a tablet or other electronic computing device being used by a medical professional), and one or more physiological data collection device holding locations 118. Generally, the compartment 114, resting surface 116, and one or more physiological data collection device holding locations 118 permit easy and efficient access to devices and other items that are used during the physiological data collection process (the details of which will be explained in connection with the explanation of FIGS. 10 and 11). In various embodiments, the compartment 114 may hold items that do not have a designated location on the exterior of the kiosk or other materials that, for various reasons, should not be stored on the exterior of the kiosk (additional details regarding the compartment 114 will be explained in association with the description of FIG. 5). For example, in one embodiment, the compartment 114 may hold physiological data collection devices that do not have designated holding locations 118 on the exterior of the exemplary kiosk 100, personal belongings of the medical professional or patient using the exemplary kiosk 100, auxiliary supplies (e.g., informational pamphlets, batteries and cables for the physiological data collection and electronic computing devices, cotton swabs, tongue depressors, gloves, other disposable medical implements, etc.), etc. Further, the resting surface 116, in various embodiments, holds an electronic computing device (e.g., computer, laptop computer, tablet, smart phone, etc.) or patient's physical medical file so that the collected physiological data may be input into the patient's medical record. Similarly, the physiological data collection device holding locations 118 hold the various physiological data collection devices (e.g., thermometer, sphygmomanometer, stethoscope, etc.) that are used during the physiological data collection process so that the medical professional may quickly and efficiently access the appropriate device (further details regarding the resting surface 116 and the physiological data collection device holding locations 118 will be explained in connection with the description of FIGS. 3 and 4).

Figure 9B:
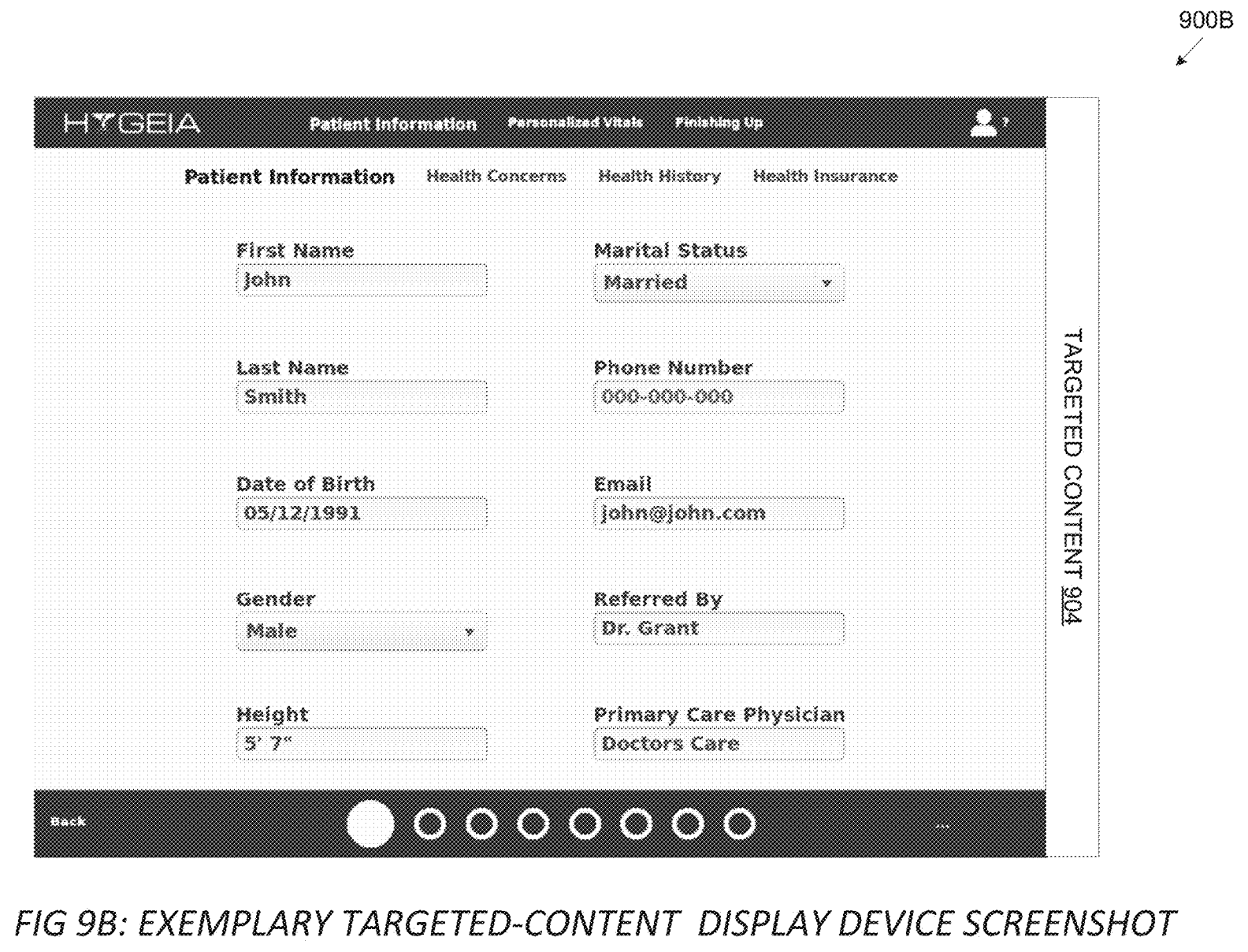

In various embodiments, exemplary kiosk 100 comprises a targeted-content display device 120 comprising a display screen 122 so that targeted content may be displayed to the patient during the physiological data collection process, during a doctor consultation (e.g., as part of a telehealth consultation, etc.), during the check-out process, etc. For example, the patient may receive targeted content regarding medicines or medical devices that are aimed at ameliorating medical conditions indicated by the patient's certain physiological data that is not within optimal ranges (e.g., high blood pressure, high temperature, etc.), devices or services that cater to a certain lifestyle of the patient (e.g., age- or gender-based targeted content, exercise equipment for individuals with physiological data within optimal ranges, etc.), etc. Accordingly, in one embodiment, the physiological data collection devices, electronic computing devices, and targeted-content display devices may be operatively connected so that physiological data is automatically collected and stored in the patient's medical record and the targeted content is displayed to the patient based on that collected data (e.g., so that the medical professional does not need to take any actions besides ensuring that a proper technique is used to collect the physiological data). Generally, the targeted-content display device 120 may be any electronic computing device (e.g., desktop computer, laptop, servers, tablets, display screens, audio speakers, etc.), combination of computing devices, software, hardware, or combination of software and hardware that is capable of running the processes disclosed herein (additional details regarding the targeted-content display device 120 will be provided in connection with the description of FIGS. 7 and 9). In one embodiment, the targeted-content display device 120 is detachable from the kiosk 100 (e.g., is a tablet, etc.) so that the patient may interact with the targeted-content display device 120 in different locations. In various embodiments, the patient is able to monitor the data collection process, provide additional information, and interact with a remote medical professional (e.g., via a video chat, etc.) through the targeted-content display device 120.

In one embodiment, the kiosk 100 is modular and may be disassembled for ease of storage or transportation. Thus, in one embodiment, when the kiosk 100 is assembled it may be reassembled in multiple configurations to suit the needs of the patient and/or medical professional, due to its modular nature. Similarly, in one embodiment, the kiosk 100 is adjustable to accommodate patients and/or medical professionals of different sizes.

Now referring to FIG. 2, an alternative perspective view 200 of a kiosk 100 is shown in accordance with one embodiment of the present disclosure. In various embodiments, the kiosk 100 may comprise a lockable drawer 202 and a lockable access panel 204 for secure ease of access to various items. Generally, the drawer 202 may hold items that do not have a designated location on the exterior of the kiosk or other materials that, for various reasons, should not be stored on the exterior of the kiosk (additional details regarding the drawer 202 will be explained in association with the description of FIG. 6). For example, in one embodiment, the drawer 202 may hold physiological data collection devices that do not have designated holding locations 118 on the exterior of the exemplary kiosk 100, personal belongings of the medical professional or patient using the exemplary kiosk 100, auxiliary supplies (e.g., informational pamphlets, batteries and cables for the physiological data collection and electronic computing devices, cotton swabs, tongue depressors, gloves, other disposable medical implements, etc.), etc. Further, in one embodiment, the drawer 202 may hold components of the targeted-content display device 120, such as a computer, audio amplifier, etc. Generally, the access panel 204 may permit access to the interior of the kiosk 100 without removing the cover of the kiosk (e.g., for maintenance, repairs, upgrades, updates, modifications, etc.).

FIG. 3 is side view 300 of a kiosk 100 in accordance with one embodiment of the present disclosure. FIG. 4 is an alternative side view 400 of a kiosk 100 in accordance with one embodiment of the present disclosure. In various embodiments, the kiosk 100 may comprise one or more physiological data collection device holding locations 118 such a thermometer holding location 302, a digital otoscope/ dermascope holding location 304, a stethoscope holding location 306, and a pulse-oximeter holding location 308. Generally, these holding locations 302, 304, 306, and 308 permit easy access to physiological data collection devices (e.g., thermometer, pulse oximeter, stethoscope, etc.) during the physiological data collection process and safely store the physiological data collection devices when they are not in use. In one embodiment, the kiosk 100 may also comprise a compartment 114 with actuating buttons 310. Generally, the compartment 114 may store items (e.g., physiological data collection devices, auxiliary supplies, etc.) that are not stored on the exterior of the kiosk 100. The actuating buttons 310, in one embodiment, may be used to operate a physiological data collection device (e.g., sphygmomanometer, etc.) that is stored within the compartment 114 without opening the compartment 114 or removing the device from the same. For example, the medical professional or patient may press one of the actuating buttons 310 to start data collection from a device stored within the compartment 114.

Referring now to FIG. 5, a perspective view 500 of an open compartment 114 of a kiosk 100 is shown in accordance with one embodiment of the present disclosure. In various embodiments, the compartment comprises a door 502 that opens to reveal the contents within the compartment 114. In one embodiment, the compartment 114 may hold physiological data collection devices 504 that do not have designated holding locations 118 on the exterior of the exemplary kiosk 100, personal belongings of the medical professional or patient using the exemplary kiosk 100, auxiliary supplies (e.g., informational pamphlets, batteries and cables for the physiological data collection and electronic computing devices, cotton swabs, tongue depressors, gloves, other disposable medical implements, etc.), etc. In one embodiment, the compartment 114 may comprise actuating buttons 310. The actuating buttons 310, in one embodiment, may be used to operate a physiological data collection device 504 (e.g., sphygmomanometer, etc.) that is stored within the compartment 114 without opening the compartment 114 or removing the device from the same. For example, the actuating buttons 310 may align with the operational buttons 506 of the physiological data collection device 504. Similarly, the kiosk 100 may comprise a port 508 that permit cables, tubes, etc. to extend from the physiological data collection device 504 to the exterior of the kiosk (e.g., a blood pressure cuff extending from the sphygmomanometer). Accordingly, the patient or medical professional may use and replace/switch the tubes extending through port 508 without accessing the physiological data collection device 504. Additionally, the kiosk 100 may comprise a dispenser 504 for dispensing certain disposable medical supplies (e.g., caps for the thermometer, pill cups, etc.).

Now referring to FIG. 6, a perspective view 600 of an open drawer 202 of a kiosk 100 is shown in accordance with one embodiment of the present disclosure. Generally, the drawer 202, which may be locked using a key 602, may hold items that do not have a designated location on the exterior of the kiosk or other materials that, for various reasons, should not be stored on the exterior of the kiosk. For example, in one embodiment, the drawer 202 may hold physiological data collection devices that do not have designated holding locations 118 on the exterior of the kiosk 100, personal belongings of the medical professional or patient using the kiosk 100, auxiliary supplies (e.g., informational pamphlets, batteries and cables for the physiological data collection and electronic computing devices, cotton swabs, tongue depressors, gloves, other disposable medical implements, etc.), etc. Further, in one embodiment, the drawer 202 may hold components of the targeted-content display device 120, such as a computer, audio amplifier, etc.

Referring now to FIG. 7, a front view 700 of a targeted-content display device 120 of a kiosk 100 is shown in accordance with one embodiment of the present disclosure. The targeted-content display device 120 may comprise, in various embodiments, a display screen 122 to display targeted content to the patient and one or more speakers 704 for projecting audio relating to the targeted content. Generally, although not shown in FIG. 7 (but potentially stored in drawer 202 from FIG. 6), the targeted-content display device 120 may be any electronic computing devices (e.g., desktop computer, laptop, servers, tablets, etc.), combination of computing devices, software, hardware, or combination of software and hardware that is capable of running the processes disclosed herein. In one embodiment, the targeted-content display device may also comprise a camera to capture still or video images of the patient and transmit them for various purposes (e.g., as part of a telehealth consultation, etc.).

Now referring to FIG. 8, an exploded view 800 of a kiosk 100, which shows its modular nature, is shown in accordance with one embodiment of the present disclosure. In various embodiments, the kiosk 100 may comprise a seat 102, an arm rest 104, one or more storage/resting locations 106 and 108 to place the patient's personal belongings, and one or more foot rests 110 and 112 to accommodate a patient during the physiological data collection process. Similarly, in various embodiments, the kiosk 100 may comprise a compartment 114, a resting surface 116, and one or more physiological data collection device holding locations 118 to facilitate the physiological data collection process. Finally, in various embodiments, the kiosk 100 may comprise a targeted-content display device 120 so that targeted content may be displayed to the patient during the physiological data collection process.

Referring now to FIG. 9 (consisting of FIGS. 9A, 9B, 9C, 9D, 9E, 9F, 9G, 9H, and 9I), screenshot of an exemplary targeted-content display device of a kiosk are shown in accordance with one embodiment of the present disclosure. Generally, a patient may view targeted content and other targeted content 902, 904, 906, 908, 910, and 912, provide information during and monitor the physiological data collection process, interact with a remote medical professional (e.g., telehealth, digital coaching, etc.), etc. through the targeted-content display device. In various embodiments, the targeted content or targeted content may be displayed on any portion or location of the screen, including, but not limited to, the top (e.g., targeted content 902), middle (e.g., targeted content 908 and 910), bottom (e.g., targeted content 912), right or left sides (e.g., targeted content 904 and 906, respectively), half of the screen (e.g., targeted content 910), all of the screen (e.g., FIG. 9H), etc.

Accordingly, FIG. 9A is a screenshot of an exemplary privacy authorization form, which a patient must provide so that the patient's protected health information can be used or disclosed for the processes described herein. FIG. 9B is a screenshot of an exemplary patient information screen from which a patient may view, provide, and/or modify their identifying information, by themselves or with the help of a medical professional. FIG. 9C is a screenshot of an exemplary health concerns screen from which a patient may view, provide, and/or modify information about the reason for their visit (e.g., current symptoms, duration of symptoms, etc.). FIG. 9D is a screenshot of an exemplary health history screen that a patient may use to view, provide, and/or modify their history of certain medical conditions (e.g., asthma, diabetes, arthritis, etc.) or habits (e.g., drinking, smoking, exercising, etc.). FIG. 9E is a screenshot of an exemplary insurance screen that a patient may use to view, provide, and/or modify their insurance information and view eligibility for consultations. FIG. 9F is a screenshot of an exemplary vitals description screen that provides the patient with information on how to perform or what to expect during the physiological data collection process. FIG. 9G is a screenshot of an exemplary vitals results screen that shows the results and/or status of the physiological data collection process. FIG. 9H is a screenshot of an exemplary remote medical professional screen that a patient could use to receive a remote diagnosis/interact with a medical professional through a video chat. Additionally, in one embodiment, FIG. 9H shows a full-screen targeted content as would be shown according to the processes described herein. FIG. 9I is a screenshot of an exemplary ratings screen wherein a patient may rate their experience using the targeted-content display device and/or kiosk.

Now referring to FIG. 10, a flowchart of an exemplary data collection process 1000 is shown according to one embodiment of the present disclosure. Generally, the exemplary data collection process 1000 is the process by which the kiosk collects physiological data regarding a patient, automatically records that data in the patient's medical records, and displays targeted content to the patient corresponding to the collected data in combination with the patient's medical background, genetic risk profiles, preferences, demographics, and other external considerations such as the location of the encounter, the weather, etc. In various embodiments, the data collection process 1000 may occur automatically with the guidance of a medical professional or through on screen prompts to the patient. In one embodiment, the data collection process 1000 may occur remotely. As will be understood by one having ordinary skill in the art, the steps and processes shown in FIG. 10 (and those of all other flowcharts shown and described herein) may operate concurrently and continuously, are generally asynchronous and independent, and are not necessarily performed in the order shown.

The data collection process 1000 begins at step 1002 when the kiosk optionally authenticates the practitioner's credentials to ensure that only authorized individuals access the kiosk. As will occur to one having ordinary skill in the art, the data collected through the data collection process 1000 is sensitive and confidential and access to this information is highly regulated. Thus, the kiosk may authenticate the practitioner's (or patient if the patient is operating the kiosk through a self-directed process) using any appropriate means (e.g., fingerprint, password, PIN number, birthdate, etc.). Once the credentials have been authenticated, the kiosk receives at step 1004, the patient identification corresponding to the patient from whom data will be collected. Generally, the patient identification may be any appropriate identifier that may be tied to an individual patient (e.g., last name and birth date, unique identifying number, fingerprint, etc.). Based on the received patient identification, the kiosk retrieves the patient records corresponding to the identified patient at step 1006. Generally, the patient records may be in physical or electronic from (e.g., electronic medical records or "EMR") and contain the patient's medical history and other relevant information (e.g., HIPAA releases, waivers, contact information, etc.).

Referring still to FIG. 10, at step 1008 the kiosk requests screening information regarding the patient from whom data will be collected. Generally, this screening information may be any information that will assist in the data collection process 1000. For example, the screening information may be updates to HIPAA releases (e.g., so that targeted content may be displayed to the patient, etc.), current symptoms, physical changes of the patient since the last visit, informational changes since the last visit (e.g., insurance, contact, etc.), etc. Thus, the kiosk receives and stores (e.g., in a system database and/or the patient's EMR) the screening information at step 1010.

Generally, the kiosk receives an indication to start the data collection process 1000 at step 1012. For example, a patient or medical practitioner may select a button on the screen of an electronic computing device or the targeted-content display device to start the initial intake process (e.g., physiological data collection process, etc.). Thus, at step 1014 in one embodiment, the kiosk determines which data to collect from the patient. The kiosk, in various embodiments, may determine which data to collect from the patient based on the patient's EMR, screening information, selection of a particular collection process, etc. As will be understood, this disclosure places no limitations on the types of physiological data that may be collected as part of the data collection process 1000 or the physiological data collection devices that may be used as part of the same.

Still referring to FIG. 10, at step 1016 according to various embodiments, the kiosk displays, via an electronic computing device or the targeted-content display device, the list of data that should be collected from the patient (e.g., height, weight, blood pressure, heart rate, temperature, blood oxygen saturation, respiratory rate, etc.). Optionally, in one embodiment, the kiosk may also provide instructions regarding how to collect the requested data at step 1018 (e.g., how to use a particular device, what the results mean, remedial instructions if the results are not accurate, etc.). These instructions may, in one embodiment, be provided via an electronic computing device or the targeted-content display device. Accordingly, in various embodiments, the kiosk receives and stores the collected data at step 1020. Generally, the kiosk may receive the collected data directly from the physiological data collection devices or through manual input from the patient or medical professional and may store the data in a system database, the patient's medical records, etc. Based on this collected data, the targeted-content display process 1100 occurs (further details regarding the targeted-content display process 1100 will be provided in association with the explanation of FIG. 11). As part of step 1020, in one embodiment, the kiosk may determine whether the collected physiological data was accurate (e.g., falls within expected ranges, etc.) or whether additional data collection is necessary (e.g., one vital sign suggests one diagnosis but requires confirmation of another uncollected vital sign). Thus, at step 1022 in various embodiments, the kiosk determines whether additional data should be collected. If additional data should be collected, the process returns to step 1018 and optionally provides instructions regarding the additional data to be collected (e.g., the medical professional may be prompted to request more information regarding a patient's medical history, etc.).

If, however, additional data will not be collected, then the process proceeds at step 1024, wherein the kiosk determines whether additional information has been requested by the patient or the medical professional. For example, a patient may request more information regarding a particular collected piece of physiological data (e.g., vital sign) or targeted content. Thus, if additional information has been requested, then, in one embodiment at step 1026, the kiosk displays (and optionally retrieves that requested information from the system database or a third party system, such as a pharmaceutical company's website) that requested information via the electronic computing device or the targeted-content display device. In one embodiment, the kiosk may transmit a message (e.g., via email, text message, etc.) to the patient and/or medical professional as part of step 1026. After displaying the requested information or if no additional information was requested, the data collection process 1000 ends.

FIG. 11 is a flowchart showing an exemplary targeted-content display process 1100 according to one embodiment of the present disclosure. Generally, the targeted-content display process 1100 is the process by which the kiosk and/or targeted-content display device displays targeted content (e.g., advertisements specifically tailored to the patient based on the collected physiological data and/or other content such as articles, news, informational flyers, etc.) to the patient. In one embodiment, the patient must have provided a HIPAA release that permits the system to conduct the targeted-content display process 1100 (e.g., as part of the data collection process 1000). In one embodiment, the patient's medical information does not leave the kiosk; instead, the kiosk conducts the steps of targeted-content display process 1100 locally and only retrieves information regarding the targeted content, targeted-content criteria, etc. from third party systems as necessary. In one embodiment, the patient's medical information is de-identified (e.g., compliant with regulatory laws, the patient's identifying information, name, address, date of birth, social security number, etc. is removed from the collected data so that only the raw data is transmitted to the systems that conduct the processes described herein) so that the targeted-content display process 1100 may be performed. Generally, it will be understood that the processes described herein are HIPAA-compliant and do not provide access to the patient's medical records to unauthorized individuals or parties. Additionally, the targeted-content display process 1100 may be interrupted or halted, such as when the medical professional consults with the patient and may be resumed at any point during the process.

In various embodiments, at step 1102, the system (or in one alternative embodiment the targeted-content display device) parses the received collected data to determine its data type (e.g., temperature, heart rate, etc.) and value (e.g., 98.6° F., 68 bpm, etc.). Based on the data type, in one embodiment at step 1104, the system retrieves targeted-content criteria corresponding to targeted content that could potentially be displayed to the patient. As will occur to one having ordinary skill in the art, the targeted-content criteria may be a particular threshold value (e.g., 100° F. for a temperature, etc.), a range (e.g., 140/90 to 159/99 mmHg for blood pressure, etc.), or a complex business rule (e.g., if a patient is female, between ages 30-45, and her mother had osteoporosis, then display a particular targeted content; if a patient is visiting for flu-like symptoms, it is January, and the patient has asthma, then display a particular targeted content). Similarly, the targeted-content criteria may indicate the priority with which certain targeted content should be displayed (e.g., based on how much an advertiser has paid, severity of the patient's symptoms, medical history of the patient, etc.); this priority may, in one embodiment, be used in step 1112 to filter and order the targeted content. Generally, the targeted-content criteria establishes certain data values that correspond to the targeted content (e.g., temperatures above 100° F. for a fever reducer, blood pressure between 140/90 and 159/99 mmHg for high blood pressure medicine, heart rates below 68 bpm for exercise equipment, etc.). Thus, at step 1106 in various embodiments, the system compares the data value to the targeted-content criteria.

At step 1108 in various embodiments, the system determines whether, based on the comparison, the targeted-content criteria are met (e.g., the patient's temperature is above 100° F., the patient's blood pressure is between 140/90 and 159/99 mmHg, etc.). If the targeted-content criteria are met, then the system retrieves, at step 1110 in various embodiments, the targeted content corresponding to the targeted-content criteria from the system database (or, in one embodiment, a third party system). In one embodiment, when multiple pieces of targeted content are retrieved, algorithms and programs may determine the duration, order, and pieces of targeted content to display at step 1112. Thus, at step 1114, the system displays that filtered targeted content, via the targeted-content display device, to the patient. Generally, the targeted content may be in any form (e.g., video, image, document, etc.) and the patient may interact with the targeted content in any manner (e.g., viewing, listening, providing information, requesting more information, etc.). Based on those interactions, in various embodiments, the system may display additional targeted content or information, request additional information for the patient from the advertiser (e.g., for immediate display, to be sent to the patient at a later date, etc.). To take these actions, the system may retrieve information (e.g., contact information, biographic information, etc.) from the patient's medical records. In one embodiment, the system may store the information regarding the targeted content that is displayed to a particular patient either locally or in a secure database system. As will be understood, this disclosure places no limitations on the types of targeted content that may be displayed as part of the targeted-content display process 1100. After displaying the targeted content or if the targeted-content criteria were not met, the targeted-content display process 1100 ends.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, some of the embodiments of the claimed inventions may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. An apparatus for collecting physiological data relating to a user, comprising:
    a generally L-shaped housing having a first lower end and a second upper end, wherein the first lower end is a base of the generally L-shaped housing and comprises a raised seat which is configured for seating of a user while physiological data relating to the user is collected, wherein the raised seat is substantially rectangular in shape and is positioned at an end of the first lower end that is distal from a vertex point of the generally L-shaped housing at which the second upper end extends vertically, wherein the raised seat comprises a weighing device operatively configured to detect a mass of the user, wherein the weighing device is operatively configured to detect a first measurement corresponding to the mass of the user in response to the user sitting on a top surface of the raised seat, wherein the raised seat comprises a foot rest operatively configured to extend out from and retract into a side of the raised seat, and wherein the weighing device is further operatively configured to detect a second measurement corresponding to the mass of the user in response to the user's feet resting upon the foot rest while the user is sitting on the top surface of the raised seat;
    a substantially rectangular armrest, wherein the substantially rectangular armrest comprises a flat top surface and a bottom surface, wherein the bottom surface is connected to a rod extending upwardly from a corner of a housing of the raised seat, wherein a total length of the rod comprises an exposed length outside the housing of the raised seat and a concealed length inside the housing of the raised seat, and wherein a height of the substantially rectangular armrest is adjustable by further extending the rod out from the corner of the housing of the raised seat and by retracting the rod into the corner of the housing of the raised seat, thereby adjusting the exposed length and concealed length of the rod;
    a substantially horizontal platform resting on the second upper end of the generally L-shaped housing, wherein the substantially horizontal platform is cantilevered with a fixed end of the substantially horizontal platform connected to the second upper end of the generally L-shaped housing, and a free end of the substantially horizontal platform extending horizontally towards the end of the first lower end that is distal from the vertex point, wherein the substantially horizontal platform houses one or more processors and electrical components operatively connected to a plurality of data collection devices, wherein the plurality of data collection devices are physically positioned on the exterior of the substantially horizontal platform to enable interaction with the user, and wherein the one or more processors are operatively configured to process data collected by the plurality of data collection devices and to determine a total mass of the user based on the first measurement and the second measurement corresponding to the mass of the user; and
    a display device extending substantially vertically from the free end of the substantially horizontal platform configured to display content to the user.

2. The apparatus of claim 1, wherein the substantially horizontal platform further comprises a compartment configured to store a device that collects data corresponding to the blood pressure of the user and is configured to permit operation of the device during collection of the data without opening the compartment.

3. The apparatus of claim 1, wherein the substantially horizontal platform further comprises a dispenser configured to dispense single-use medical supplies for use while the physiological data is collected.

4. The apparatus of claim 1, wherein the display device further comprises a substantially pentagonal housing, and wherein an upper corner of the substantially pentagonal housing comprises a receptacle to store a thermometer.

5. The apparatus of claim 1, wherein the plurality of data collection devices comprise a thermometer, a pulse oximeter, a sphygmomanometer, a stethoscope, a digital otoscope, and a digital dermascope.

6. The apparatus of claim 1, wherein a separate weighing device is operatively configured to detect a third measurement corresponding to the mass of the user in response to the user standing on a top surface of the first lower end physically located between the vertex point and the raised seat, wherein the third measurement corresponding to the mass of the user comprises the total mass of the user.

\* \* \* \* \*